(12) United States Patent
Albert et al.

(10) Patent No.: US 7,964,733 B2
(45) Date of Patent: Jun. 21, 2011

(54) ALKYL SULFOXIDE QUINOLINES AS NK-3 RECEPTOR LIGANDS

(75) Inventors: Jeffrey S. Albert, Wilmington, DE (US); Gerard M. Koether, Wilmington, DE (US); Cristobal Alhambra, Wilmington, DE (US); James Kang, Wilmington, DE (US); Thomas R. Simpson, Wilmington, DE (US); James Woods, Wilmington, DE (US); Yan Li, Wilmington, DE (US)

(73) Assignee: AstraZeneca AB, Södertälje (SE)

(*) Notice: Subject to any disclaimer, the term of this patent is extended or adjusted under 35 U.S.C. 154(b) by 487 days.

(21) Appl. No.: 12/067,572

(22) PCT Filed: Sep. 19, 2006

(86) PCT No.: PCT/SE2006/001068
§ 371 (c)(1),
(2), (4) Date: Apr. 21, 2008

(87) PCT Pub. No.: WO2007/035158
PCT Pub. Date: Mar. 29, 2007

(65) Prior Publication Data
US 2008/0214605 A1 Sep. 4, 2008

Related U.S. Application Data

(60) Provisional application No. 60/719,275, filed on Sep. 21, 2005, provisional application No. 60/719,286, filed on Sep. 21, 2005.

(51) Int. Cl.
*C07D 215/38* (2006.01)
(52) U.S. Cl. ......................... 546/169; 514/312; 514/313
(58) Field of Classification Search .................. 546/169; 514/311, 312
See application file for complete search history.

(56) References Cited

U.S. PATENT DOCUMENTS

| | | | | |
|---|---|---|---|---|
| 5,811,553 | A * | 9/1998 | Farina et al. | 546/153 |
| 6,335,448 | B1 * | 1/2002 | Sisko et al. | 546/169 |
| 6,355,654 | B1 * | 3/2002 | Giardina et al. | 514/312 |
| 6,432,977 | B1 * | 8/2002 | Giardina et al. | 514/311 |
| 6,608,083 | B1 * | 8/2003 | Farina et al. | 514/311 |
| 7,482,458 | B2 * | 1/2009 | Farina et al. | 546/169 |
| 2005/0096316 | A1 | 5/2005 | Farina et al. | |
| 2008/0234269 | A1 * | 9/2008 | Campbell et al. | 514/235.2 |
| 2008/0306110 | A1 * | 12/2008 | Albert et al. | 514/312 |

FOREIGN PATENT DOCUMENTS

| | | |
|---|---|---|
| EP | 0940391 A2 | 9/1999 |
| GB | 2302689 A | 1/1997 |
| WO | 9532948 | 12/1995 |
| WO | 9602509 | 2/1996 |
| WO | 9624582 A1 | 8/1996 |
| WO | 9719926 A1 | 6/1997 |
| WO | 9721680 A1 | 6/1997 |
| WO | 9852942 A1 | 11/1998 |
| WO | 0031037 A1 | 6/2000 |
| WO | 0064877 A1 | 11/2000 |
| WO | 0238548 A1 | 5/2002 |
| WO | 0243734 A1 | 6/2002 |
| WO | 0244165 A1 | 6/2002 |
| WO | 02083645 A1 | 10/2002 |
| WO | 02083663 A1 | 10/2002 |
| WO | 2005014575 A1 | 2/2005 |
| WO | 2006050989 A1 | 5/2006 |
| WO | 2006050991 A1 | 5/2006 |
| WO | 2006050992 | 5/2006 |
| WO | 2006137789 A1 | 12/2006 |
| WO | 2007039123 | 4/2007 |
| WO | 2007044251 | 4/2007 |

OTHER PUBLICATIONS

Guiseppe A. M. Giardina, et al, "Discovery of a novel class of selective non-peptide antagonists for the human neurokinin-3 receptor. 2. Identification of (S)-N-(1-phenylpropyl)-3-hydroxy-2-phenylquinoline-4-carbosamide (SB 223412)", J. Med. Chem., 1999, 42, pp. 1053-1065.

Frank E. Blaney, et al, "Stepwise Modulation of Neurokinin-3 and Neurokinin-2 Receptor Affinity and Selectivity in Quinoline Tachykinin Receptor Antagonists", J. Med. Chem. 2001, vol. 44, pp. 1675-1689, scheme 1 and table 1.

Stanislaw Biniecki, et al; "Synteza Beta-Fenyloetyloamidu oraz 2-I 3-Pikoliloamidow Kvasu 2-Fenylocynchoninowego"; Acta Poloniae Pharmaceutica, No. 3, vol. 34, 1977, pp. 271-273.

* cited by examiner

*Primary Examiner* — D. Margaret Seaman
(74) *Attorney, Agent, or Firm* — Connolly Bove Lodge & Hutz LLP

(57) ABSTRACT

Compounds of Formula I

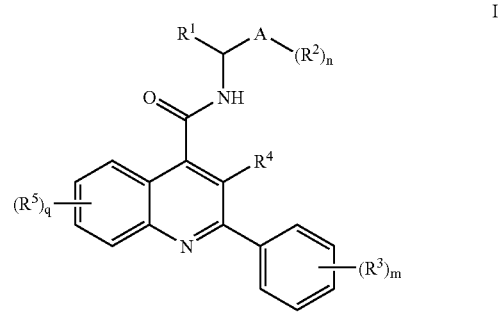

wherein $R^1$, A, $R^2$, $R^3$, $R^4$, $R^5$, n, m and q are as described in the specification, pharmaceutically-acceptable salts, methods of making, pharmaceutical compositions containing and methods for using the same.

8 Claims, No Drawings

ALKYL SULFOXIDE QUINOLINES AS NK-3 RECEPTOR LIGANDS

This is a National Phase of PCT/SE2006/001068 filed Sep. 19, 2006, which claims the priority of Provisional Application No. 60/719,275 filed Sep. 21, 2005, and Provisional Application No. 60/719,286 filed Sep. 21, 2005.

FIELD OF THE INVENTION

This invention relates to quinoline derivatives, pharmaceutical compositions comprising them, and the use of such compounds in the treatment of central nervous system and peripheral diseases or disorders. This invention also relates to the use of such compounds in combination with one or more other CNS agents to potentiate the effects of the other CNS agents. The compounds of this invention are also useful as probes for the localization of cell surface receptors.

BACKGROUND OF THE INVENTION

Tachykinin receptors are the targets of a family of structurally related peptides which include substance P (SP), neurokinin A (NKA) and neurokinin B (NKB), collectively "tachykinins." Tachykinins are synthesized in the central nervous system (CNS), and peripheral tissues, where they exert a variety of biological activities. Three tachykinin receptors are known which are named neurokinin-1 (NK-1), neurokinin-2 (NK-2) and neurokinin-3 (NK-3) receptors. NK-1 and NK-2 receptors are expressed in a wide variety of peripheral tissues and NK-1 receptors are also expressed in the CNS whereas NK-3 receptors are primarily expressed in the CNS.

The neurokinin receptors mediate a variety of tachykinin-stimulated biological effects that include: transmission of excitatory neuronal signals in the CNS and periphery (e.g. pain signals), modulation of smooth muscle contractile activity, modulation of immune and inflammatory responses, induction of hypotensive effects via dilation of the peripheral vasculature, and stimulation of endocrine and exocrine gland secretions.

In the CNS, activation of NK-3 receptors has been shown to modulate dopamine, acetylcholine and serotonin release, suggesting a therapeutic utility for NK-3 ligands for the treatment of a variety of disorders including anxiety, depression, schizophrenia and obesity. Studies in primate brain have shown the presence of NK-3 mRNA in a variety of regions relevant to these disorders. Studies in rats have shown NK-3 receptors to be located on MCH-containing neurons in the lateral hypothalamus and zona incerta, again suggesting a therapeutic utility for NK-3 ligands for obesity.

Non-peptide ligands have been developed for each of the tachykinin receptors, however known non-peptide SK-3 receptor antagonists suffer from a number of problems such as species selectivity which limits the potential to evaluate these compounds in many appropriate disease models. New non-peptide NK-3 receptor ligands are therefore desirable for use as therapeutic agents and as tools to investigate the biological consequences of NK-3 receptor modulation.

SUMMARY OF THE INVENTION

Disclosed are compounds, particularly quinoline derivatives with affinity for NK-3 receptors (NK-3r). These compounds have potential for the treatment of a broad array of diseases, disorders and conditions including but not limited to depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer in which modulation of the activity of NK-3 receptors is beneficial.

Ligands for NK-3 receptors disclosed and stereoisomers, enantiomers, in vivo-hydrolysable precursors and pharmaceutically-acceptable salts thereof are compounds of Formula I,

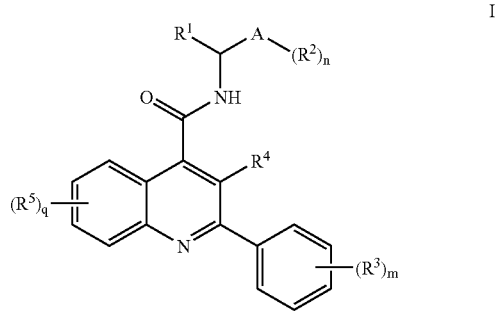

wherein:
$R^1$ is selected from H, $C_{1-4}$alkyl-, $C_{3-6}$cycloalkyl- and $C_{1-4}$alkylOC(O)—;
A is phenyl or $C_{3-7}$cycloalkyl-;
$R^2$ at each occurrence is independently selected from H, —OH, —NH$_2$, —CN, halogen, $C_{1-6}$alkyl-, $C_{3-7}$cycloalkyl-, $C_{1-6}$alkoxy- and $C_{1-6}$alkoxyC$_{1-6}$alkyl-;
n is 1, 2 or 3;
$R^3$ at each occurrence is independently selected from H, —OH, —NH$_2$, —NO$_2$, —CN, halogen, $C_{1-6}$alkyl-, $C_{1-6}$alkoxy- and $C_{1-6}$alkoxyC$_{1-6}$alkyl-;
m is 1, 2 or 3;
$R^4$ is E-S(O)$_r$—(CH$_2$)$_p$—, wherein E is selected from $C_{1-6}$alkyl-, $C_{3-6}$cycloalkyl-, aryl- and heteroaryl-, p is selected from 0, 1, 2, 3, 4, 5 and 6, and r is selected from 0, 1 and 2;
$R^5$ at each occurrence is independently selected from H, —OH, —CN, halogen, —$R^6$, —OR$^6$, —NR$^6$R$^7$, —SR$^6$, —SOR$^6$ and —SO$_2$R$^6$;
q is 1, 2 or 3;
wherein:
$R^6$ and $R^7$ at each occurrence are independently selected from H, a $C_{1-6}$ straight or branched alkyl group, a $C_{2-6}$ straight or branched alkenyl or alkynyl group and a $C_{3-7}$carbocyclic group having zero, one or two double- or triple-bonds, wherein said groups are either unsubstituted or substituted with one or more moieties selected from —OH, =O, —NH$_2$, —CN, halogen, aryl and $C_{1-3}$alkoxy-;
and,
when $R^1$, $R^2$ or $R^3$ is an alkyl, cycloalkyl, alkoxy or alkoxyalkyl moiety, said moieties are unsubstituted or have 1, 2, 3, 4 or 5 substituents independently selected at each occurrence from —OH, —NH$_2$, —CN, phenyl and halogen.

Also disclosed are pharmaceutical compositions and formulations containing the compounds, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes. In particular are disclosed compounds, compositions containing them, and methods using them for treating or preventing conditions and disorders associated with a wide range of diseases or disorders in which NK-3 receptors are considered to have a role.

DETAILED DESCRIPTION OF THE INVENTION

Compounds of the invention are compounds of Formula I.

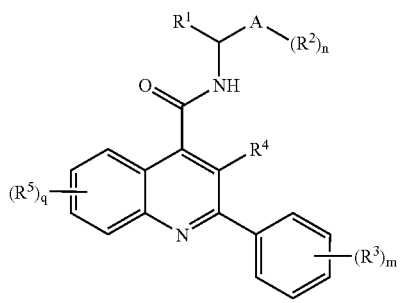

wherein:
$R^1$ is selected from H, $C_{1-4}$alkyl-, $C_{3-6}$cycloalkyl- and $C_{1-4}$alkylOC(O)—;

A is phenyl or $C_{3-7}$cycloalkyl-;

$R^2$ at each occurrence is independently selected from H, —OH, —NH$_2$, —CN, halogen, $C_{1-6}$alkyl-, $C_{3-7}$cycloalkyl-, $C_{1-6}$alkoxy- and $C_{1-6}$alkoxyC$_{1-6}$alkyl-;

n is 1, 2 or 3;

$R^3$ at each occurrence is independently selected from H, —OH, —NH$_2$, —NO$_2$, —CN, halogen, $C_{1-6}$alkyl-, $C_{1-6}$alkoxy- and $C_{1-6}$alkoxyC$_{1-6}$alkyl-;

m is 1, 2 or 3;

$R^4$ is E-S(O)$_r$—(CH$_2$)$_p$—, wherein E is selected from $C_{1-6}$alkyl-, $C_{3-6}$cycloalkyl-, aryl- and heteroaryl-, p is selected from 0, 1, 2, 3, 4, 5 and 6, and r is selected from 0, 1 and 2;

$R^5$ at each occurrence is independently selected from H, —OH, —CN, halogen, —R$^6$, —OR$^6$, —NR$^6$R$^7$, —SR$^6$, —SOR$^6$ and —SO$_2$R$^6$;

q is 1, 2 or 3;

wherein:
$R^6$ and $R^7$ at each occurrence are independently selected from H, a $C_{1-6}$ straight or branched alkyl group, a $C_{2-6}$ straight or branched alkenyl or alkynyl group and a $C_{3-7}$carbocyclic group having zero, one or two double- or triple-bonds, wherein said groups are either unsubstituted or substituted with one or more moieties selected from —OH, =O, —NH$_2$, —CN, halogen, aryl and $C_{1-3}$alkoxy-;

and, when $R^1$, $R^2$ or $R^3$ is an alkyl, cycloalkyl, alkoxy or alkoxyalkyl moiety, said moieties are unsubstituted or have 1, 2, 3, 4 or 5 substituents independently selected at each occurrence from —OH, —NH$_2$, —CN, phenyl and halogen;

stereoisomers, enantiomers, in vivo-hydrolysable precursors and pharmaceutically-acceptable salts thereof.

Particular compounds are those wherein:
A is phenyl;
$R^1$ is selected from $C_{1-4}$alkyl-, $C_{3-6}$cycloalkyl- and $C_{1-4}$alkylOC(O)—;
$R^2$ is selected from H, halogen and unsubstituted $C_{1-6}$alkoxy-;
$R^3$ is H or halogen;
n and m are both 1, and
when $R^1$ is an alkyl, cycloalkyl, alkoxy or alkoxyalkyl moiety, said moieties are unsubstituted or have 1, 2, 3, 4 or 5 substituents independently selected at each occurrence from —OH, —NH$_2$, —CN and halogen;

stereoisomers, enantiomers, in vivo-hydrolysable precursors and pharmaceutically-acceptable salts thereof.

Other particular compounds are those wherein:
A is phenyl;
$R^1$ is selected from $C_{1-4}$alkyl- and $C_{3-6}$cycloalkyl-;
$R^2$ is selected from H, halogen and unsubstituted $C_{1-6}$alkoxy-;
$R^3$ is H or halogen;
n and m are both 1;
$R^4$ is E-S(O)$_r$—(CH$_2$)$_p$—, wherein E is selected from $C_{1-6}$alkyl-, $C_{3-6}$cycloalkyl-, aryl- and heteroaryl-, p is selected from 0, 1, 2 and 3 and r is selected from 0, 1 and 2;
$R^5$ is H;
stereoisomers, enantiomers, in vivo-hydrolysable precursors and pharmaceutically-acceptable salts thereof.

Still other particular compounds are those wherein:
A is phenyl;
$R^1$ is ethyl or cyclopropyl;
$R^2$ is selected from H, F and —OCH$_3$;
$R^3$ is H or F;
n, m and q are each 1;
$R^4$ is E-S(O)$_r$—(CH$_2$)$_p$—, wherein E is selected from $C_{1-6}$alkyl-, $C_{3-6}$cycloalkyl-, aryl- and heteroaryl-, p is selected from 0, 1, 2 and 3 and r is selected from 0, 1 and 2;
$R^5$ at each occurrence is independently selected from H, —OH and halogen;
stereoisomers, enantiomers, in vivo-hydrolysable precursors and pharmaceutically-acceptable salts thereof.

Still other particular compounds are enantiomers in accord with Formula II

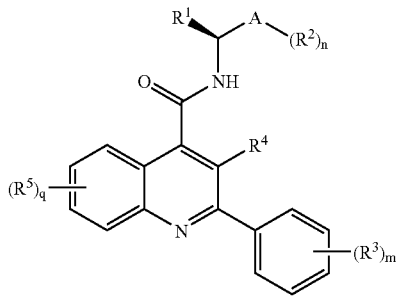

wherein $R^1$, A, $R^2$, n, $R^3$, m, $R^4$, $R^5$ and q are as defined for Formula I;

stereoisomers, enantiomers, in vivo-hydrolysable precursors and pharmaceutically-acceptable salts thereof.

Particular compounds are selected from those described in Table 1, stereoisomers, enantiomers, in vivo-hydrolysable precursors and pharmaceutically-acceptable salts thereof.

Compounds of the present invention have the advantage that they may be more soluble, be more easily absorbed and more efficacious in vivo, produce fewer side effects, be less toxic, be more potent, more selective, be longer acting, be less metabolized and/or have a better pharmacokinetic profile than, or have other useful pharmacological or physicochemical properties over known compounds. Using assays for functional activity described herein, compounds of the invention will be found to have IC50's of less than about 1 μM for NK-3 receptors and many compounds will be found to have IC50's of less than about 100 nM for NK-3 receptors.

ABBREVIATIONS AND DEFINITIONS

As used herein, unless otherwise indicated, $C_{1-6}$alkyl includes but is not limited to methyl, ethyl, n-propyl, n-butyl, i-propyl, i-butyl, t-butyl, s-butyl moieties, whether alone or part of another group and alkyl groups may be straight-chained or branched.

As used herein, unless otherwise indicated, $C_{1-6}$alkoxy includes but is not limited to —O-methyl, —O-ethyl, —O-n-propyl, —O-n-butyl, —O-i-propyl, —O-i-butyl, —O-t-butyl, —O-s-butyl moieties, whether alone or part of another group and alkoxy groups may be straight-chained or branched.

As used herein $C_{3-6}$cycloalkyl groups include but are not limited to the cyclic alkyl moieties cyclopropyl, cyclobutyl, cyclopentyl and cyclohexyl.

As used herein, unless otherwise indicated, $C_{2-6}$alkenyl includes but is not limited to 1-propenyl, 2-propenyl, 1-butenyl, 2-butenyl and 3-butenyl.

As used herein, unless otherwise indicated, $C_{2-6}$alkynyl includes but is not limited to ethynyl, 1-propynyl, 2-propynyl, 1-butynyl, 2-butynyl and 3-butynyl.

As used herein, unless otherwise indicated, halo or halogen refers to fluorine, chlorine, bromine, or iodine;

As used herein, aryl includes to phenyl and naphthyl;

As used herein, aromatic or non-aromatic heterocyclic rings include but are not limited to N- or C-linked furyl, imidazolyl, oxazolyl, pyrrolidinyl, thiazolyl, thiophenyl, pyrrolyl, morpholinyl, piperidinyl, piperazinyl, pyrazinyl, pyridyl, pyrimidinyl, indanyl, indolyl, quinolinyl, isoquinolinyl, quinazolinyl, quinoxalinyl, benzo[b]thiophenyl, benzoxazolyl, or benzthiazolyl;

DCM refers to dichloromethane;

EtOAc refers to ethyl acetate;

EDC refers to 1-(3-dimethylaminopropyl)-3-ethylcarbodiimide;

EDTA refers to ethylenediaminetetraacetic acid;

HEPES refers to 4-(2-hydroxyethyl)-1-piperazine ethane sulfonic acid, monosodium salt, and TEA refers to triethylamine.

In processes described herein, where necessary, hydroxy, amino, or other reactive groups may be protected using a protecting group as described in the standard text "Protecting groups in Organic Synthesis", $3^{rd}$ Edition (1999) by Greene and Wuts.

Unless otherwise stated, reactions are conducted under an inert atmosphere, preferably under a nitrogen atmosphere and are usually conducted at a pressure of about one to about three atmospheres, preferably at ambient pressure (about one atmosphere).

The compounds of the invention and intermediates may be isolated from their reaction mixtures by standard techniques.

Acid addition salts of the compounds of Formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of Formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

Certain compounds of Formula I may exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Synthesis and Schemes

Compounds of Formula I may be prepared by general methods.

Method 1:

As shown in Schemes A and B, a 3-methyl-2-phenyl-quinoline-4-carboxylic acid (alkyl)-amide may be reacted with N-bromosuccinimide (NBS) in the presence of a radical initiator such as ultraviolet light to afford a 3-bromomethyl-2-phenyl-quinoline-4-carboxylic acid (alkyl)-amide. Said alkylhahide may be reacted with a thiol such as sodium methanethiolate to afford the corresponding thioether; which may then be oxidized with an oxidizing agent such as sodium periodate to afford a corresponding 3-methanesulfinylmethyl-2-phenyl-quinoline-4-carboxylic acid (alkyl)-amide. Alternatively, said thioether may be oxidized with an oxidizing agent such as meta-chloroperoxybenzoic acid to afford a corresponding 3-methanesulfonylmethyl-2-phenyl-quinoline-4-carboxylic acid (alkyl)-amide.

Method 2:

Compounds with ethyl or other alkyl-linked tethers between the quinoline and the sulfur atom can be prepared by reacting a 3-bromomethyl-2-phenyl-quinoline-4-carboxylic acid (alkyl)-amide with another nucleophile such as dimsyl potassium, instead of sodium methanethiolate, to afford a corresponding 3-(2-methylsulfanyl-ethyl)-2-phenyl-quinoline-4-carboxylic acid (alkyl)-amide. This material can then be oxidized according to the processes described in Method 1 to afford a corresponding sulfone.

Method 3:

Compounds where a sulfur is directly attached to the quinoline can be prepared, as shown in Scheme B, by reacting a 3-alkylsulfanyl-2-phenyl-quinoline-4-carboxylic acid with an appropriate amine in the presence of a suitable coupling agent system such as dicyclohexylcarbodiimide and hydroxybenzotriazole to afford a 3-alkylsulfanyl-2-phenyl-quinoline-4-carboxylic acid (alkyl)-amide, this compound may be oxidized with an oxidizing agent such as sodium periodate to afford a corresponding sulfoxide, or with an oxidizing agent such as meta-chloroperoxybenzoic acid to afford a corresponding sulfone.

An exemplary process, to form a particular compound of Formula I is shown in Schemes A and B.

Scheme A.
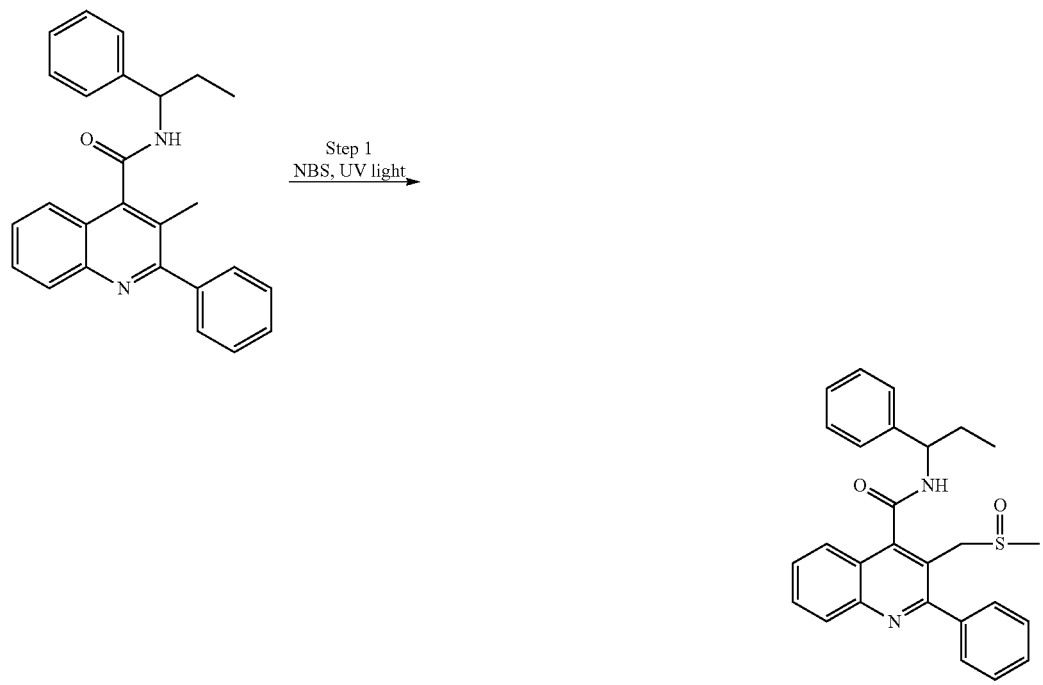
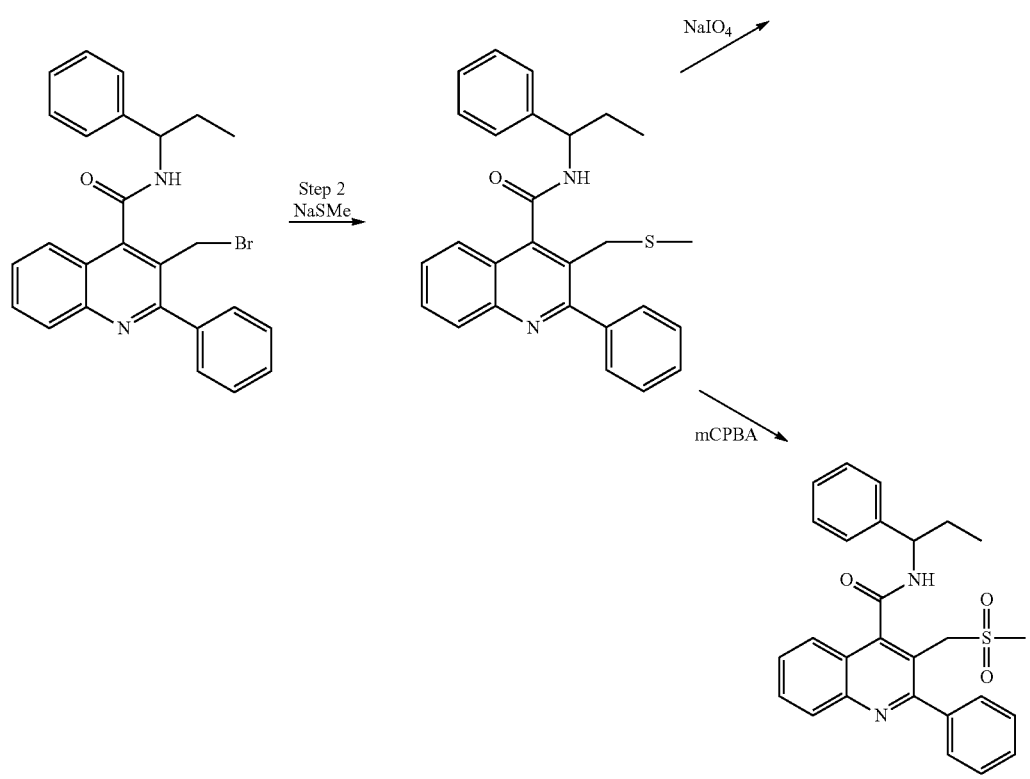

Scheme B.

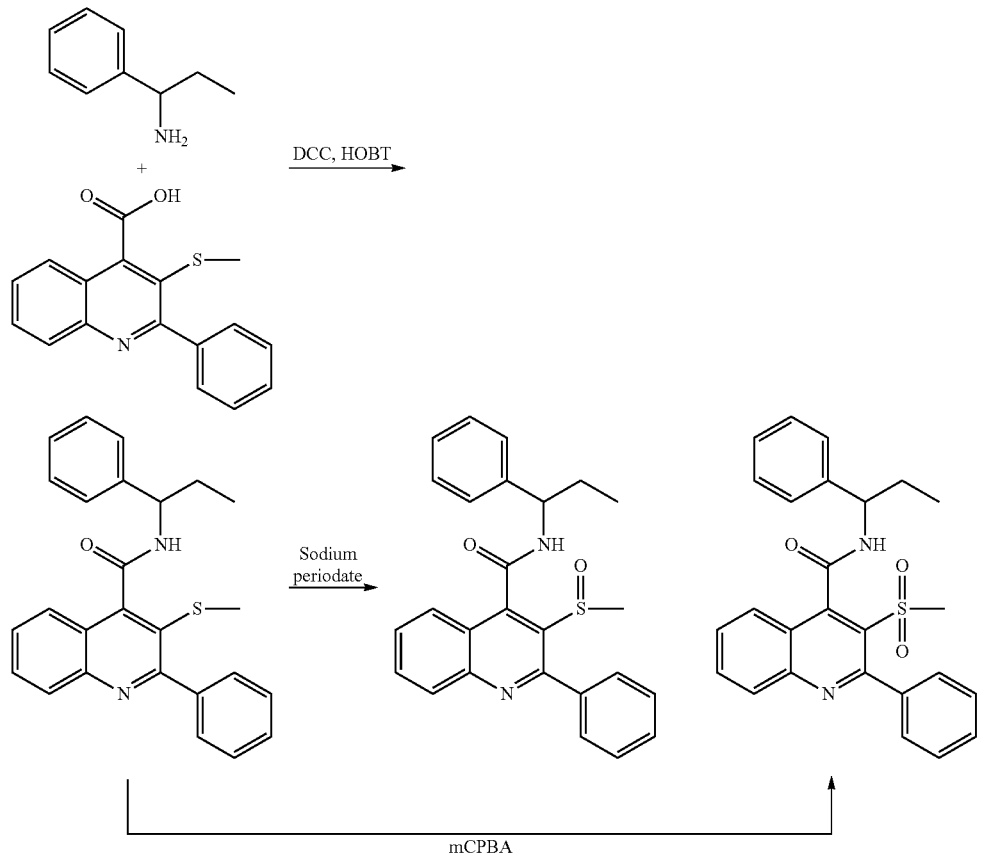

Thus as illustrated in Scheme A, 3-methyl-2-phenyl-quinoline-4-carboxylic acid (1-phenyl-propyl)-amide may be halogenated by reaction with a halogen source such as N-bromosuccinimide in the presence of a radical initiator such as ultraviolet light at elevated temperature (typically 50-100° C.) in an appropriate solvent such as carbon tetrachloride to afford 3-bromomethyl-2-phenyl-quinoline-4-carboxylic acid (1-phenyl-propyl)-amide. This material may be reacted with a suitable nucleophile such as sodium methanethiolate to afford 3-(methylthiomethyl)-2-phenyl-N-(1-phenylpropyl)quinoline-4-carboxamide. This material may be oxidized with an oxidizing agent such as sodium periodate to afford 3-(methylsulfinylmethyl)-2-phenyl-N-(1-phenyl-propyl)quinoline-4-carboxamide; or it may be oxidized with an oxidizing agent such as meta-chloroperoxybenzoic acid to afford 3-(methylsulfonylmethyl)-2-phenyl-N-(1-phenylpro-pyl)quinoline-4-carboxamide.

In a further aspect the invention relates to compounds described herein wherein one or more of the atoms is a radio-isotope of the same element. In a particular form of this aspect of the invention the compound is labeled with tritium. Such radio-labeled compounds are synthesized either by incorporating radio-labeled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Compounds of the invention labeled with tritium are useful for the discovery of novel medicinal compounds which bind to and modulate the activity, by agonism, partial agonism, or antagonism, of an NK-3 receptor. Such tritium-labeled compounds may be used in assays that measure the displacement of such compounds to assess the binding of ligands that bind to NK-3 receptors.

In a further aspect the invention relates to compounds described herein additionally comprising one or more atoms of a radioisotope. In a particular form of this aspect of the invention the compound comprises a radioactive halogen. Such radio-labeled compounds are synthesized by incorporating radio-labeled starting materials by known methods. Particular embodiments of this aspect of the invention are those in which the radioisotope is selected from $^{18}F$, $^{123}I$, $^{125}I$, $^{131}I$, $^{75}Br$, $^{76}Br$, $^{77}Br$ or $^{82}Br$. A most particular embodiment of this aspect of the invention is that in which the radioisotope is $^{18}F$. Such compounds comprising one or more atoms of a radioisotope are useful as positron emission tomography (PET) ligands and for other uses and techniques to determine the location of NK3 receptors.

Therapeutic Uses of Compounds:

In another aspect the invention relates to compounds in accord with Formula I described herein and the use of such compounds in therapy and in compositions useful for therapy.

In another aspect the invention encompasses the use of compounds described herein for the therapy of diseases mediated through the action of NK-3 receptors. Such an aspect encompasses methods of treatment or prophylaxis of diseases or conditions in which modulation of the NK-3 receptor is beneficial which methods comprise administering a therapeutically-effective amount of an antagonistic compound of the invention to a subject suffering from said disease or condition.

One embodiment of this aspect of the invention is a method of treatment or prophylaxis of disorders, wherein the disorder is depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, or testicular cancer comprising administering a pharmacologically effective amount of a compound of Formula I to a patient in need thereof.

A further aspect of the invention is the use of a compound according to the invention, an enantiomer thereof or a pharmaceutically-acceptable salt thereof, in the treatment or prophylaxis of a disease or condition in which modulation of the NK-3 receptor is beneficial. Particular diseases and conditions that may be treated are depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer. More particular embodiments encompass uses of a compound in the treatment or prophylaxis of anxiety, depression, schizophrenia and obesity.

A further aspect of the invention is the use of a compound according to the invention, an enantiomer thereof or a pharmaceutically-acceptable salt thereof, in the manufacture of a medicament for the treatment or prophylaxis of the diseases or conditions mentioned herein. A particular embodiment of this aspect of the invention is the use of a compound of the invention in the manufacture of a medicament for treatment or prophylaxis of depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer.

Pharmaceutical Compositions

Compounds of the invention, enantiomers thereof, and pharmaceutically-acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically-acceptable diluent, lubricant or carrier.

Examples of Diluents, Lubricants and Carriers are:
  for tablets and dragees: lactose, starch, talc, stearic acid;
  for capsules: tartaric acid or lactose;
  for injectable solutions: water, alcohols, glycerin, vegetable oils;
  for suppositories: natural or hardened oils or waxes.

There is also provided a process for the preparation of such a pharmaceutical composition which process comprises mixing or compounding the ingredients together and forming the mixed ingredients into tablets or suppositories, encapsulating the ingredients in capsules or dissolving the ingredients to form injectable solutions.

Pharmaceutically-acceptable derivatives include solvates and salts. For example, the compounds of the invention may form acid addition salts with acids, such as conventional pharmaceutically-acceptable acids including maleic, hydrochloric, hydrobromic, phosphoric, acetic, fumaric, salicylic, citric, lactic, mandelic, tartaric and methanesulfonic acids.

Acid addition salts of the compounds of Formula I which may be mentioned include salts of mineral acids, for example the hydrochloride and hydrobromide salts; and salts formed with organic acids such as formate, acetate, maleate, benzoate, tartrate, and fumarate salts. Acid addition salts of compounds of Formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

For the uses, methods, medicaments and compositions mentioned herein the amount of compound used and the dosage administered will, of course, vary with the compound employed, the mode of administration and the treatment desired. However, in general, satisfactory results are obtained when the compounds of the invention are administered at a daily dosage of about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carriers, lubricants and diluents.

Some compounds of the invention may exist in tautomeric, enantiomeric, stereoisomeric or geometric isomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions which will not cause racemization.

Exemplary compounds of the invention may be prepared by processes analogous to that described in Scheme A. Those of skill in the art will readily appreciate that many suitable amines and acid chlorides and carboxylic acids may be used to form compounds within the scope of the subject matter described herein as Formula I.

EXEMPLARY COMPOUNDS
Examples 1, 2 and 3 were prepared in accord with Scheme 1
Scheme 1:
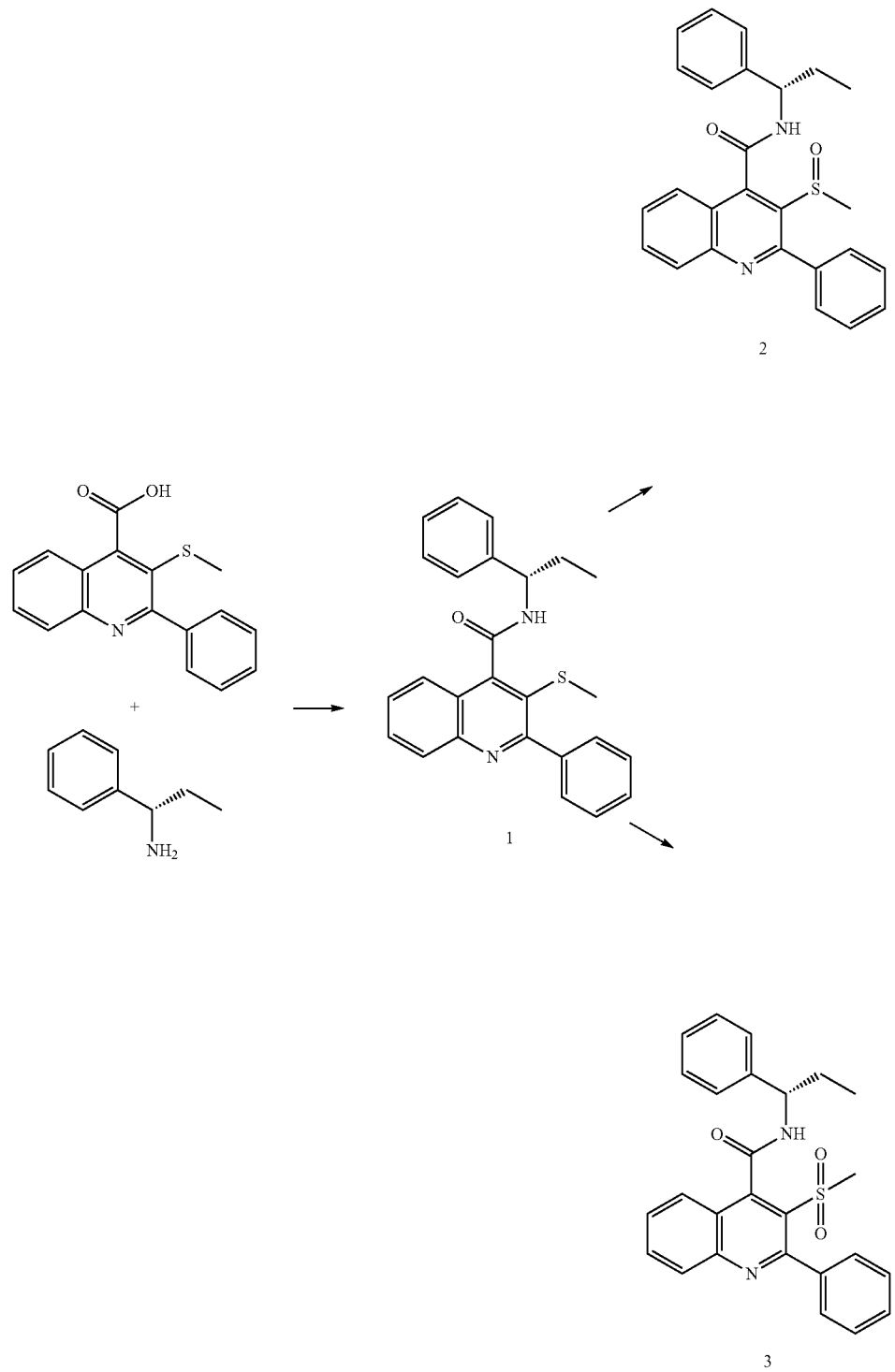

Example 1

3-(methylthio)-2-phenyl-N-[(1S)-1-phenylpropyl]quinoline-4-carboxamide (1)

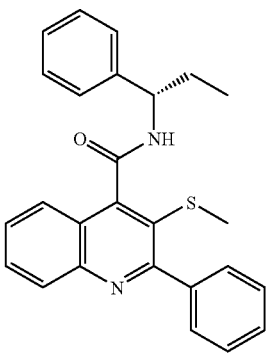

To a solution of 3-(methylthio)-2-phenylquinoline-4-carboxylic acid (150 mg, 0.51 mmol) and triethylamine (0.17 mL, 1.22 mmol) in EtOAc (2.5 mL) at 5° C. was added thionyl chloride (0.043 mL, 0.61 mmol). The cooling bath was removed and the suspension allowed to stir for 0.5 h, then (S)-(−)-1-phenylpropylamine (76 mg, 0.56 mmol) was added and reaction allowed to stir for another 0.5 h. Water (2 mL) and EtOAc (2 mL) were then added, the layers shaken together, then separated, the organics dried over $Na_2SO_4$, filtered, and concentrated under reduced pressure. The resulting material was purified by silica gel chromatography (0-20% EtOAc/$CH_2Cl_2$) to give the desired product (150 mg, 70% yield) as a solid. $^1$H NMR (300 MHz, $CDCl_3$) δ 8.11 (d, J=8.4 Hz, 1H), 7.78-7.67 (m, 4H), 7.55-7.27 (m, 9H), 6.12 (d, J=8.5 Hz, 1H), 5.30 (q, J=7.6 Hz, 1H), 2.16-1.91 (m, 5H), 1.06 (t, J=7.4 Hz, 3H); HRMS m/z 413.1669, calcd 413.1688.

Example 2

3-(methylsulfinyl)-2-phenyl-N-[(1S)-1-phenylpropyl]quinoline-4-carboxamide (2)

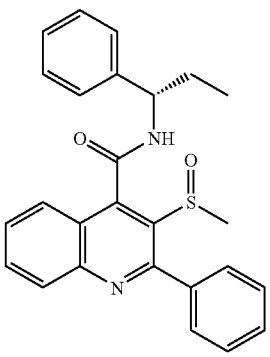

A solution of 3-(methylthio)-2-phenyl-N-[(1S)-1-phenylpropyl]quinoline-4-carboxamide (1) (60 mg, 0.145 mmol) in EtOH (2 mL) was prepared and to this, with stirring, was added a solution of $NaIO_4$ (37 mg, 0.174 mmol) in $H_2O$ (1 mL). Additional $H_2O$ (1 mL) and EtOH (2 mL) were then added and reaction heated at 50° C. for 2 h. Additional $NaIO_4$ (10 mg) was then added and reaction heated at 78° C. for 14 h. Again, more $NaIO_4$ (50 mg) was added and reaction heated at 90° C. (sealed tube) for 3 h., then allowed to cool. It was concentrated under reduced pressure, diluted with EtOAc, washed with $H_2O$, dried over $Na_2SO_4$, filtered, and again concentrated under reduced pressure. The resulting material was purified by silica gel chromatography to give the desired products (50 mg, 80% yield) as a solid. ($^1$HNMR shows two diastereomers present). $^1$H NMR (300 MHz, $CDCl_3$) δ 8.20-7.28 (m, 14H), 6.96-6.48 (m, 1H), 5.31-5.15 (m, 1H), 2.94-2.62 (m, 3H), 2.32-1.84 (m, 2H), 1.07-0.90 (m, 3H); HRMS m/z 429.1602, calcd 429.1637.

Example 3

3-(methylsulfonyl)-2-phenyl-N-[(1S)-1-phenylpropyl]quinoline-4-carboxamide (3)

To a stirring solution of 3-(methylthio)-2-phenyl-N-[(1S)-1-phenylpropyl]quinoline-4-carboxamide (1) (40 mg, 0.097 mmol) in $CH_2Cl_2$ (1 mL) was added MCPBA (54 mg of 70-75%, 0.23 mmol) and solution allowed to stir for 1 h. Additional MCPBA (10 mg) was added and reaction heated at 40° C. for 1 h., then allowed to cool. Next was added $H_2O$ (1 mL) and a few crystals of sodium thiosulfate, $CH_2Cl_2$ (3 mL), and 1 N NaOH (2 mL-aqueous). The layers were shaken together, separated, the organics dried over $Na_2SO_4$, filtered, and concentrated under reduced pressure. The residue was purified by silica gel chromatography (0-25% EtOAc/$CH_2Cl_2$) to give the desired product (6 mg) as a white solid. $^1$H NMR (300 MHz, $CDCl_3$, 65° C.) δ 8.13 (d, J=8.5 Hz, 1H), 7.92-7.76 (m, 2H), 7.59-7.25 (m, 11H), 6.19-6.08 (m, 1H), 5.27-5.15 (m, 1H), 2.96 (s, 3H), 2.28-1.87 (m, 2H), 1.00 (t, J=7.4 Hz, 3H); HRMS m/z 445.1573, calcd 445.1586.

Example 4, 5, 6 and 7 were prepared in accord with Scheme 2.
Scheme 2:
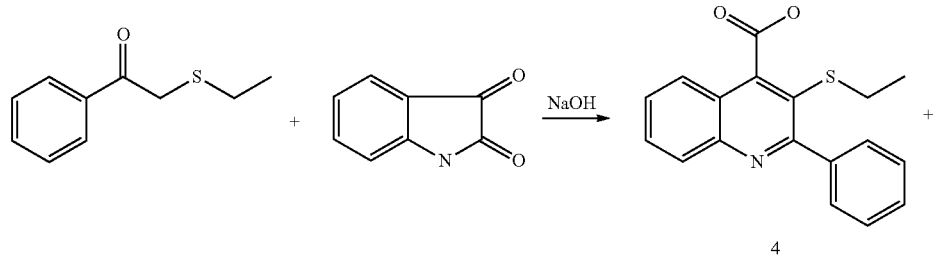
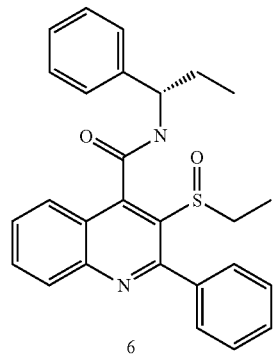
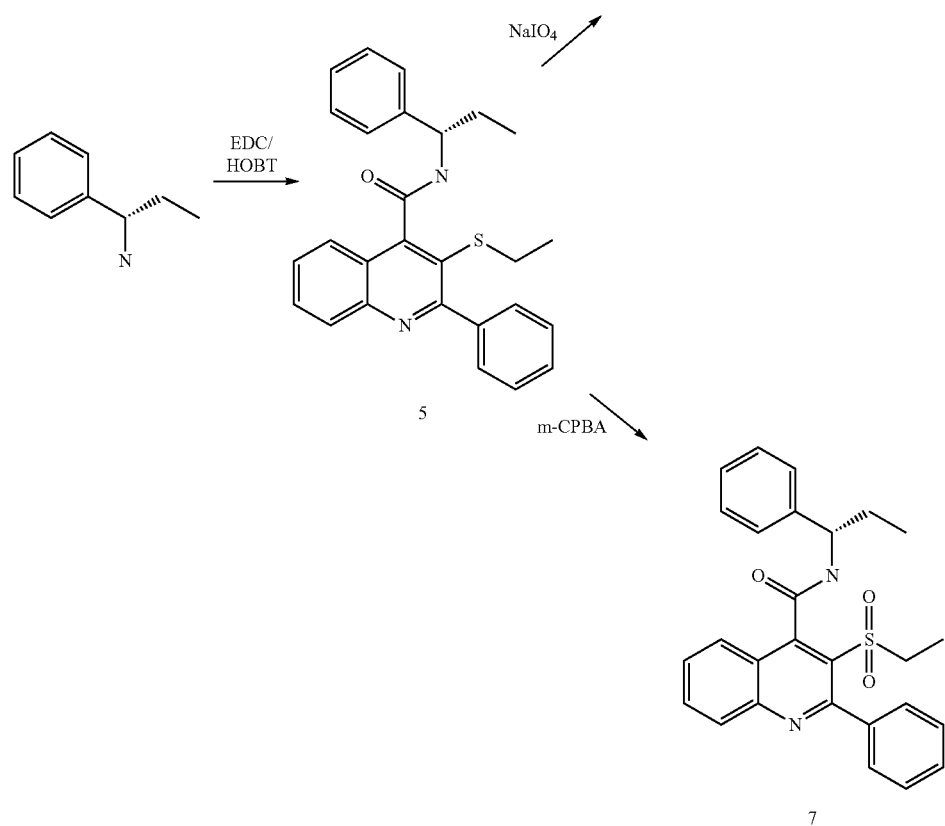

Example 4

3-(ethylthio)-2-phenyl-N-[(1S)-1-phenylpropyl]quinolin-4-carboxamide (5)

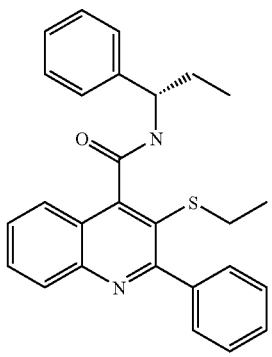

A solution of 3-(ethylthio)-2-phenylquinoline-4-carboxylic acid (4) (269 mg, 0.87 mmol), HOBT hydrate (230 mg, 1.5 mmol), 4-methylmorpholine (164 μL, 1.5 mmol) in DCM (30 ml) was added EDC (289 mg, 1.5 mmol) at RT under $N_2$. (S)-1-Phenyl propylamine (202 mg, 1.5 mmol) was then added and the reaction mixture stirred at RT for 12 h. All solvent was removed in vacuo and the residue was partitioned between ethyl acetate and 0.5 N HCl aqueous solution. The organic phase was washed with 10% aqueous sodium bicarbonate solution, brine, and dried over sodium sulfate. The organic solution was then concentrated in vacuo. The residue was purified by chromatography eluting with 15-25% ethyl acetate/hexane to give the title compound (315 mg, 85% yield) as a solid. $^1$H NMR (300 MHz, $CDCl_3$) δ 0.96 (t, 3H), 1.22 (t, 3H), 2.0 (m, 2H), 2.40 (m, 2H), 5.28 (q, 1H), 7.20 (d, 2H), 7.34 (d, 2H), 7.39 (m, 2H), 7.78 (m, 2H), 7.84 (m, 2H), 8.00 (m, 1H), 8.11 (m, 2H), 8.15 (m, 2H). MS APCI, m/z=427 (M+1). LCMS: 2.82 min.

The starting acid, 3-(ethylthio)-2-phenylquinoline-4-carboxylic acid (4), was prepared in the following manner:

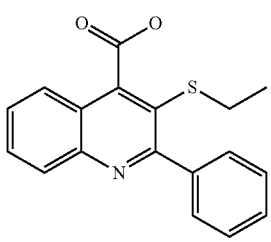

4

To isatin (882 mg, 6 mmol) was added a solution of sodium hydroxide (2.30 g, 57.5 mmol) in water (5.0 mL). The resulting brown precipitate was stirred vigorously at rt for 20 minutes before being heated to 85° C. A solution of 2-(ethylthio)-1-phenylethanone (1080 mg, 6.0 mmol) in ethanol)THF/water (13 mL/2.5 mL/13 mL was then added dropwise over 30 minutes. The reaction mixture was stirred at 85° C. or further 4 h before cooling to rt. All organic solvents were removed in vacuo and the aqueous residue reduced to a volume of approximately 12 mL. The aqueous residue was washed with ether (3×10 mL) and then the aqueous residue was acidified with cooling to pH 4 with concentrated acetic acid. The precipitate formed were collected, washed with water and dried to give the title compound as a solid (1580 mg, 85.2%). $^1$H NMR (300 MHz, $CDCl_3$) δ 1.22 (t, 3H), 2.97 (q, 2H), 7.28 (d, 1H), 7.35 (d, 2H), 7.77 (m, 1H), 7.86 (m, 1H), 7.99 (m, 2H), 8.29 (m, 1H), 9.11 (m, 1H), 10.33 (b, 2H). MS APCI, m/z=310 (M+11). LCMS: 1.73 min.

Example 5

3-(ethylsulfiny)-2-phenyl-N-[(S)-1-phenylpropyl]quinoline-4-carboxamide (6)

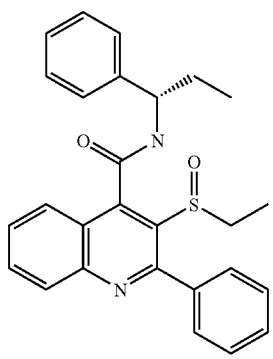

To a solution of 3-(ethylthio)-2-phenyl-N-[(1S)-1-phenylpropyl]quinolin-4-carboxamide (5) (300 mg, 0.70 mmol) in MeOH (25 mL) was added a solution of $NaIO_4$ (300 mg, 1.4 mmol) in water (15 mL) while it was cooled to 0° C. The cooling bath was removed, and reaction allowed stir for 12 h. LCMS indicated no reaction take place. Added another 2 eq of $NaIO_4$ and the reaction mixture was heated to reflux for 8 h. It was then diluted with EtOAc, washed with brine, dried over $Na_2SO_4$, filtered, and concentrated under reduced pressure. The residue was purified by silica gel chromatography (10-35% EtOAc/$CH_2Cl_2$) to give the desired product (two diastereomers) as a solid (88 mg, 28.4%). $^1$H NMR (300 MHz, $CDCl_3$) δ 0.97 (t, 3H), 1.21 (t, 3H), 2.01 (m, 2H), 2.71 (m, 2H), 5.21 (q, 1H), 7.21 (d, 2H), 7.34 (d, 2H), 7.39 (m, 2H), 7.78 (m, 2H), 7.84 (m, 2H), 8.00 (m, 1H), 8.11 (m, 2H), 8.14 (m, 1H), 8.16 (m, 1H). MS APCI, m/z=443 (M+1). LCMS: 2.15 min.

Example 6

3-(ethylsulfony)-2-phenyl-N-[(S)-1-phenylpropyl]quinoline-4-carboxamide (7)

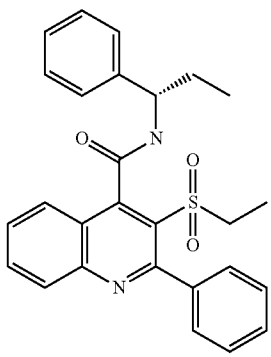

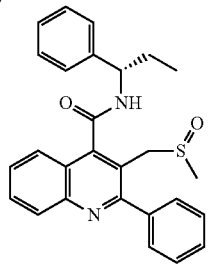

10

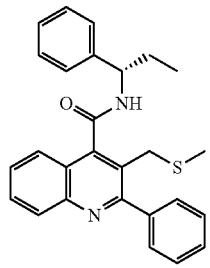

9

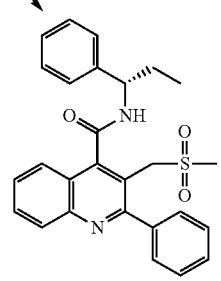

11

To a solution of 3-(ethylthio)-2-phenyl-N-[(1S)-1-phenylpropyl]quinolin-4-carboxamide (5) (100 mg, 0.235 mmol) in CH$_2$Cl$_2$ (10 mL) was treated with m-CPBA (112 mg, 70-75%, 0.45 mmol) at 0° C. The cooling bath was removed, and reaction allowed stir for 12 h. LCMS indicated the reaction only goes for 60%. Another 30 mg of m-CPBA added and continue to stir the mixture for 6 h. It was then diluted CH$_2$Cl$_2$, washed with 1N NaOH aqueous solution, brine, dried over Na$_2$SO$_4$, filtered, and concentrated under reduced pressure. The residue was purified by silica gel chromatography (10-15% EtOAc/hexane) to give the desired product as a solid (40 mg, 38.4%). $^1$H NMR (300 MHz, CDCl$_3$) δ 0.98 (t, 3H), 1.26 (t, 3H), 2.15 (m, 2H), 2.96 (m, 2H), 5.22 (m, 1H), 7.22 (d, 2H), 7.36 (d, 2H), 7.39 (m, 2H), 7.78 (m, 2H), 7.84 (m, 2H), 8.00 (m, 1H), 8.11 (m, 2H), 8.14 (m, 1H), 8.17 (m, 1H). MS APCI, m/z=459 (M+1). LCMS: 2.27 min.

Examples 7, 8, 9 and 10 were prepared in accord with Scheme 3.

Scheme 3.

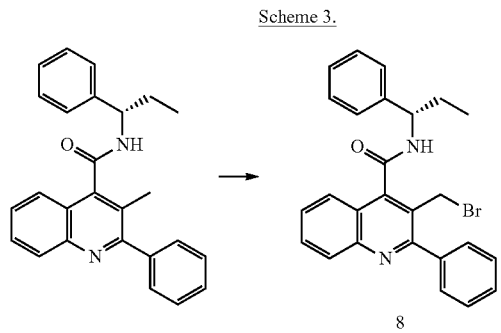

8

Example 7

3-(bromomethyl)-2-phenyl-N-[(1S)-1-phenylpropyl]quinoline-4-carboxamide (8)

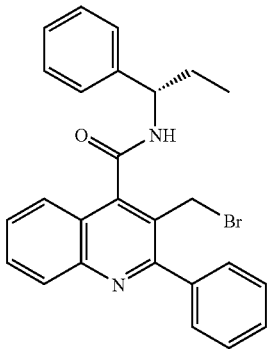

3-methyl-2-phenyl-N-[(1S)-1-phenylpropyl]quinoline-4-carboxamide (9.8 g, 26 mmol) was dissolved in 200 mL hot CCl$_4$ (with stirring) under N$_2$ and heated at a gentle reflux. NBS (6.9 g, 39 mmol) was added and solution irradiated with long wave UV light for 0.5 h. Additional NBS (1.9 g, 11 mmol) was added and solution irradiated and refluxed for another 0.5 h. It was then allowed to cool and concentrated under reduced pressure to remove most of the CCl$_4$. The residue was then dissolved in CH$_2$Cl$_2$ and washed with aqueous NaHCO$_3$ containing a few crystals of sodium thiosulfate. The organic layer was then dried over Na$_2$SO$_4$, filtered, and concentrated under reduced pressure. The resulting material was then purified using silica gel chromatography (0-15% EtOAc/CH$_2$Cl$_2$) to give 2.9 g of desired product (24%) as a yellow-white solid. $^1$H NMR (300 MHz, CDCl$_3$, 52° C.) δ 8.11 (d, J=8.1 Hz, 1H), 7.81-7.67 (m, 2H), 7.67-7.58 (m, 2H), 7.55-7.26 (m, 9H), 6.39 (d, J=7.8 Hz, 1H), 5.28 (q, J=7.6 Hz, 1H), 4.74-4.50 (m, 2H), 2.23-1.91 (m, 2H), 1.03 (t, J=7.4 Hz, 3H); LCMS: m/z 459 (MH$^+$).

Example 8

3-[(methylthio)methyl]-2-phenyl-N-[(1S)-1-phenyl-propyl]quinoline-4-carboxamide (9)

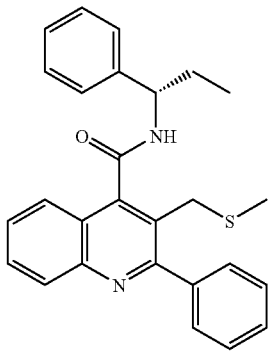

To a stirring solution of 3-(bromomethyl)-2-phenyl-N-[(1S)-1-phenylpropyl]quinoline-4-carboxamide (8) (2.9 g, 6.32 mmol) in anhydrous THF (35 mL) under N$_2$ was added sodium thiomethoxide (NaSMe, 880 mg, 12.64 mmol) and reaction stirred 1.5 h. It was then diluted with EtOAc; washed with aqueous 0.3 N NaOH, then H$_2$O, then brine; dried over Na$_2$SO$_4$; filtered; and concentrated under reduced pressure. The residue was purified by silica gel chromatography (5-15% EtOAc/CH$_2$Cl$_2$) to give the desired product (2.5 g, 90% yield) as a solid. $^1$H NMR (300 MHz, CDCl$_3$, 52° C.) δ 8.10 (d, J=8.4 Hz, 1H), 7.78 (d, J=8.1 Hz, 1H), 7.72-7.60 (m, 3H), 7.53-7.25 (m, 9H), 6.68 (d, J=7.8 Hz, 1H), 5.29 (q, J=7.6 Hz, 1H), 3.79 (q, J=13.7 Hz, 2H), 2.19-1.90 (m, 2H), 1.77 (s, 3H), 1.03 (t, J=7.4 Hz, 3H); LCMS: m/z 427 (MH$^+$).

Example 9

3-[(methylsulfinyl)methyl]-2-phenyl-N-[(1S)-1-phenylpropyl]quinoline-4-carboxamide (10)

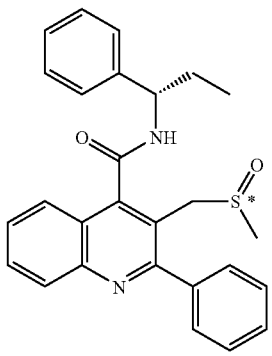

A solution of 3-[(methylthio)methyl]-2-phenyl-N-[(1S)-1-phenylpropyl]quinoline-4-carboxamide (9)(1.7 g, 3.98 mmol) in EtOH (40 mL) was cooled to 0° C., and to this, with stirring, was added a solution of NaIO$_4$ (1.02 g, 4.78 mmol) in H$_2$O (20 mL). The cooling bath was removed and reaction allowed to stir for 3 h, and then concentrated under reduced pressure to remove most of the EtOH. It was then diluted with EtOAc, washed with H$_2$O (containing some NaCl to reduce emulsion), dried over Na$_2$SO$_4$, filtered, and concentrated under reduced pressure. The residue was purified by silica gel chromatography (10-35% EtOAc/CH$_2$Cl$_2$) to give the desired products (two diastereomers) each as a solid.

Isomer A: $^1$H NMR (300 MHz, CDCl$_3$, 52° C.) δ 8.66 (d, J=6.6 Hz, 1H), 8.11 (d, J=8.4 Hz, 1H), 8.02 (d, J=7.6 Hz, 1H), 7.73 (t, J=8.4 Hz, 1H), 7.62-7.51 (m, 3H), 7.50-7.25 (m, 8H), 5.31 (q, J=8.0 Hz, 1H), 3.96 (s, 2H), 2.10-1.90 (m, 5H), 1.04 (t, J=7.3 Hz, 3H); LCMS: m/z 443 (MH$^+$).

Isomer B: $^1$H NMR (300 MHz, CDCl$_3$, 52° C.) δ 8.43 (d, J=7.6 Hz, 1H), 8.09 (d, J=8.1 Hz, 1H), 7.75-7.64 (m, 2H), 7.57-7.26 (m, 1H), 5.20 (q, J=7.6 Hz, 1H), 4.25 (q, J=16.7 Hz, 2H), 2.43 (b, 3H), 2.20-1.88 (m, 2H), 1.00 (t, J=7.4 Hz, 3H); LCMS: m/z 443 (MH$^+$).

Example 10

3-[(methylsulfonyl)methyl]-2-phenyl-N-[(1S)-1-phenylpropyl]quinoline-4-carboxamide (11)

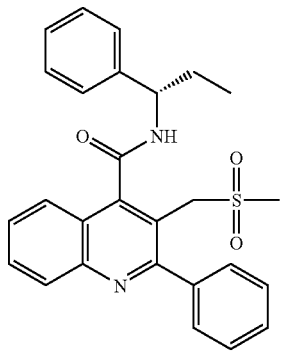

To a stirring solution of 3-[(methylthio)methyl]-2-phenyl-N-[(1S)-1-phenylpropyl]quinoline-4-carboxamide (9) (800 mg, 1.87 mmol) at 0° C. was added MCPBA (900 mg, 70-75%, 4.31 mmol), the cooling bath removed, and reaction allowed to stir for 1 h. Additional MCPBA (100 mg) was added and reaction heated briefly to 40° C., then allowed to cool. Sodium thiosulfate (Na$_2$S$_2$O$_3$.5H$_2$O-1.5 g) and H$_2$O (10 mL) were added and suspension stirred vigorously for 10 min., diluted with CH$_2$Cl$_2$, washed with aqueous 0.3 N NaOH, dried over Na$_2$SO$_4$, filtered, and concentrated under reduced pressure. The residue was purified by silica gel chromatography (0-25% EtOAc/CH$_2$Cl$_2$) to give the desired product (630 mg, 73% yield) as a solid. $^1$HNMR (300 MHz, CDCl$_3$, 52° C.) δ 8.12 (d, J=8.4 Hz, 1H), 7.83-7.68 (m, 2H), 7.61 (d, J=7.7 Hz, 2H), 7.56-7.26 (m, 10H), 5.22 (q, J=7.6 Hz, 1H), 4.74 (d, J=12.3 Hz, 2H), 2.31 (s, 3H), 2.20-1.88 (m, 2H), 1.00 (t, J=7.4 Hz, 3H); LCMS: m/z 459 (MH$^+$).

Examples 11 and 12 were prepared in accord with Scheme 4.

Scheme 4.

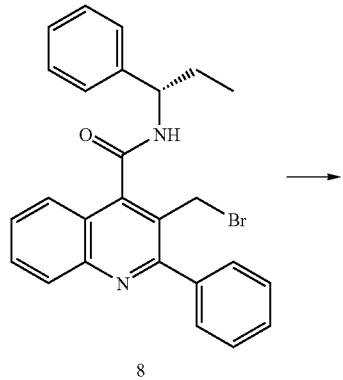

8

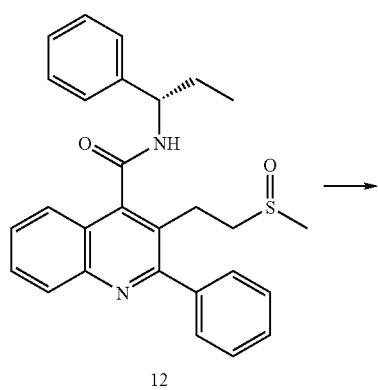

12

Example 11

3-[2-(methylsulfinyl)ethyl]-2-phenyl-N-[(1S)-1-phenylpropyl]quinoline-4-carboxamide (12)

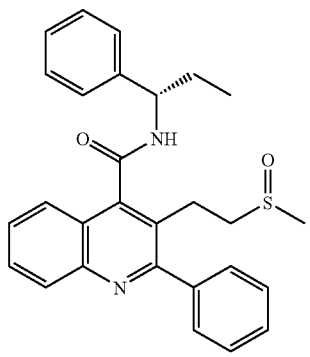

A solution of DMSO (0.075 mL, 1.05 mmol) and HMPA (0.38 mL, 2.2 mmol) in anhydrous THF (3 mL) was prepared under $N_2$ and cooled to −78° C. To this was added a solution of n-BuLi (0.71 mL, 1.6 M in hexanes, 1.13 mmol), the reaction allowed to stir for 10 min., then 3-(bromomethyl)-2-phenyl-N-[(1S)-1-phenylpropyl]quinoline-4-carboxamide (8) (200 mg, 0.44 mmol) was added as a solution in anhydrous THF (1 mL). The reaction was allowed to stir 10 min., additional anhydrous THF (1 mL) added, and reaction allowed stirring another 10 min. The cooling bath was then removed, saturated aqueous $NH_4Cl$ (1 mL), $H_2O$ (1 mL), and $Et_2O$ (1 mL) added, the layers shaken together, and then separated. The organics were then dried over $Na_2SO_4$, filtered, and concentrated under reduced pressure. The residue was purified by silica gel chromatography (EtOAc/$CH_2Cl_2$) to give the desired product (170 mg, 85% yield) as a solid. $^1$H NMR (300 MHz, $CDCl_3$, 52° C.) δ 8.10 (d, J=8.0 Hz, 1H), 7.86-7.61 (m, 2H), 7.55-7.25 (m, 12H), 5.29-5.16 (m, 1H), 3.44-3.07 (m, 2H), 2.73-2.37 (m, 2H), 2.27-2.15 (m, 3H), 2.15-1.86 (m, 2H), 1.02 (t, J=7.4 Hz, 3H); LCMS: m/z 457 (MH$^+$). HRMS m/z 457.1927, calcd. 457.1950.

Example 12

3-[2-(methylsulfonyl)ethyl]-2-phenyl-N-[(1S)-1-phenylpropyl]quinoline-4-carboxamide (13)

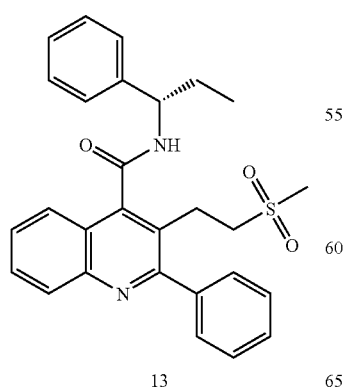

13

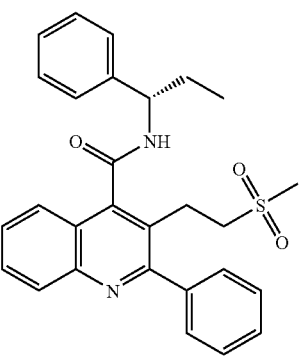

To a stirring solution of 3-[2-(methylsulfinyl)ethyl]-2-phenyl-N-[(1S)-1-phenylpropyl]quinoline-4-carboxamide (12) (60 mg, 0.13 mmol) in $CH_2Cl_2$ at 0° C. was added MCPBA (70-75%, 36 mg, 0.16 mol). The cooling bath was removed and reaction stirred for 2 h, then sodium thiosulfate (1.2 eq.) and $H_2O$ (1 mL) were added and suspension stirred until all solids had dissolved. Aqueous 1 N NaOH (1 mL) and $CH_2Cl_2$ (2 mL) were then added, the layers shaken together, separated, the organics dried over $Na_2SO_4$, filtered, and concentrated under reduced pressure. The residue was purified by silica gel chromatography (5-20% $EtOAc/CH_2Cl_2$) to give the desired product (40 mg, 65% yield) as a solid. $^1$H NMR (300 MHz, $CDCl_3$, 52° C.) δ 8.12 (d, J=8.2 Hz, 1H), 7.78-7.65 (m, 2H), 7.56-7.26 (m, 11H), 6.31 (d, J=7.7 Hz, 1H), 5.23 (q, J=7.6 Hz, 1H), 3.36-2.88 (m, 4H), 2.45-2.34 (m, 3H), 2.16-1.88 (m, 2H), 1.04 (t, J=7.4 Hz, 3H); HRMS m/z 473.1878, calcd 473.1899.

Example 13

3-[(isopropylthio)methyl]-2-phenyl-N-[(1S)-1-phenylpropyl]quinoline-4-carboxamide

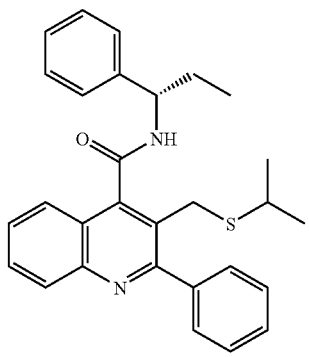

This compound was prepared similarly to 3-[(methylthio)methyl]-2-phenyl-N-[(1S)-1-phenylpropyl]quinoline-4-carboxamide (9, Scheme 3) except sodium 2-propane thiolate was used instead of sodium thiomethoxide. (Excess sodium 2-propane thiolate was added and reaction heated at 65° C. for 1 h to effect conversion.) $^1$H NMR (300 MHz, $CDCl_3$, 52° C.) δ 8.09 (d, J=8.4 Hz, 1H), 7.78 (d, J=8.5 Hz, 1H), 7.71-7.61 (m, 3H), 7.54-7.25 (m, 9H), 6.69 (d, J=7.7 Hz, 1H), 5.28 (q, J=7.5 Hz, 1H), 3.91-3.72 (m, 2H), 2.61-2.48 (m, 1H), 2.20-1.90 (m, 2H), 1.08-0.91 (m, 9H); HRMS m/z 455.2127, calcd 455.2157.

Example 14

2-phenyl-N-[(1S)-1-phenylpropyl]-3-[(pyridin-4-ylthio)methyl]quinoline-4-carboxamide

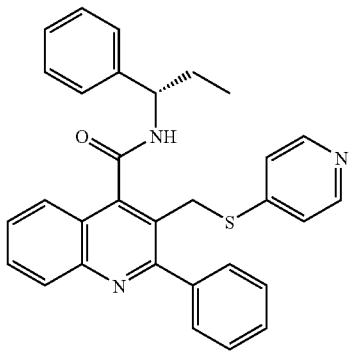

3-(bromomethyl)-2-phenyl-N-[(1S)-1-phenylpropyl]quinoline-4-carboxamide (8) (150 mg, 0.33 mmol) was dissolved in $CH_3CN$ (2 mL) under $N_2$ and to this, with stirring, was added $K_2CO_3$ (140 mg, 0.99 mmol), then 4-mercaptopyridine (40 mg, 0.36 mmol). The suspension was allowed to stir overnight; concentrated; diluted with EtOAc; washed with 0.5 N NaOH, then $H_2O$; dried over $Na_2SO_4$; filtered, and concentrated under reduced pressure. The residue was purified by silica gel chromatography ($EtOAc/CH_2Cl_2$) to afford the desired product as oil (120 mg, 74% yield). $^1$H NMR (300 MHz, $CDCl_3$, 52° C.) δ 8.30 (s, 2H), 8.14 (d, J=8.4 Hz, 1H), 7.80 (d, J=7.2 Hz, 1H), 7.76-7.69 (m, 1H), 7.62-7.49 (m, 3H), 7.43-7.37 (m, 3H), 7.35-7.28 (m, 2H), 7.25-7.19 (m, 3H), 6.80 (d, J=4.4 Hz, 2H), 6.37 (d, J=7.9 Hz, 1H), 5.21 (q, J=7.6 Hz, 1H), 4.36-4.23 (m, 2H), 2.08-1.82 (m, 2H), 0.95 (t, J=7.4 Hz, 3H); HRMS m/z 490.1931, calcd 490.1953.

Example 15

3-[(isopropylsulfinyl)methyl]-2-phenyl-N-[(1S)-1-phenylpropyl]quinoline-4-carboxamide

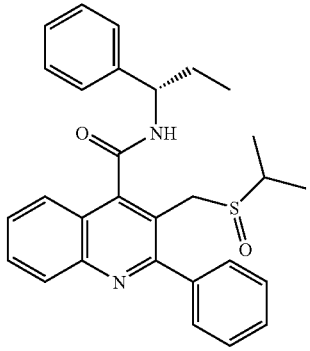

This compound [two diastereomers] was prepared similarly to 3-[(methylsulfinyl)methyl]-2-phenyl-N-[(1S)-1-phenylpropyl]quinoline-4-carboxamide (2, scheme 1) except 3-[(isopropylthio)methyl]-2-phenyl-N-[(1S)-1-phenylpropyl]quinoline-4-carboxamide (Example 13) was used instead of 3-[(methylthio)methyl]-2-phenyl-N-[(1S)-1-phenylpropyl]quinoline-4-carboxamide (1). $^1$H NMR (300 MHz, CDCl$_3$) δ 8.90-8.68 (m, 1H), 8.16-8.03 (m, 2H), 7.80-7.27 (m, 12H), 5.35-5.12 (m, 1H), 4.30-3.67 (m, 2H), 2.86-1.83 (m, 3H), 1.19-0.55 (m, 9H); HRMS m/z 471.2077, calcd 471.2106.

Example 16

2-phenyl-N-[(1S)-1-phenylpropyl]-3-[(pyridin-4-ylsulfinyl)methyl]quinoline-4-carboxamide

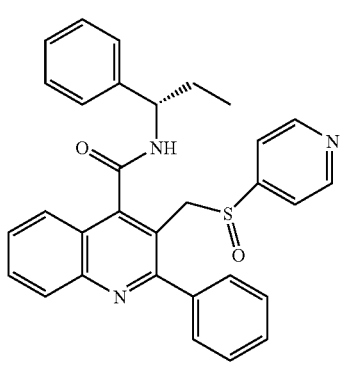

This compound [two diastereomers, TFA salt] was prepared similarly to 3-[(methylsulfinyl)methyl]-2-phenyl-N-[(1S)-1-phenylpropyl]quinoline-4-carboxamide (2) except 2-phenyl-N-[(1S)-1-phenylpropyl]-3-[(pyridin-4-ylthio)methyl]quinoline-4-carboxamide (Example 14) was used instead of 3-[(methylthio)methyl]-2-phenyl-N-[(1S)-1-phenylpropyl]quinoline-4-carboxamide (1). (Excess NaIO$_4$ was added and reaction heated to effect conversion. Product was purified using reverse phase HPLC.) $^1$H NMR (300 MHz, CDCl$_3$, 52° C.) δ 8.81-8.43 (m, 2H), 8.23-8.12 (m, 2H), 8.08-7.90 (m, 1H), 7.86-7.73 (m, 2H), 7.71-7.26 (m, 12H), 7.11-7.03 (m, 1H), 6.69-6.61 (m, 1H), 5.32-5.15 (m, 1H), 4.50-4.11 (m, 2H), 2.21-1.94 (m, 2H), 1.08-0.95 (m, 3H); LCMS: m/z 506 (MH$^+$).

Example 17

3-[(isopropylsulfonyl)methyl]-2-phenyl-N-[(1S)-1-phenylpropyl]quinoline-4-carboxamide

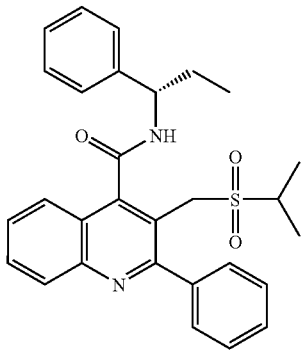

This compound was isolated as a secondary product in the preparation of 3-[(isopropylthio)methyl]-2-phenyl-N-[(1S)-1-phenylpropyl]quinoline-4-carboxamide (Example 13). $^1$H NMR (300 MHz, CDCl$_3$, 52° C.) δ 8.11 (d, J=8.4 Hz, 1H), 7.88-7.25 (m, 14H), 5.28-5.15 (m, 1H), 4.76-4.51 (m, 2H), 2.61-2.43 (m, 1H), 2.21-1.88 (m, 2H), 1.09-0.86 (m, 9H); HRMS m/z 487.2008, calcd 487.2055.

The exemplary compounds in Table 1 and the processes describe the invention by way of illustration and example for clarity of understanding. However to those skilled in the art, upon contemplation of the teaching of compounds, processes and methods of this invention, modifications and changes will be apparent that may be made thereto without departing from the spirit or scope of the invention.

TABLE 1

| Example | Structure | Name |
|---|---|---|
| 18 | 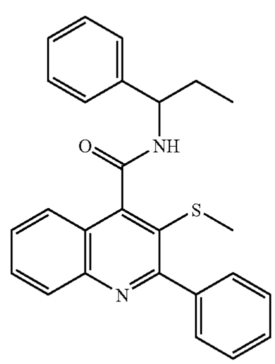 | 3-(methylthio)-2-phenyl-N-(1-phenylpropyl)quinoline-4-carboxamide |

TABLE 1-continued

| Example | Structure | Name |
|---|---|---|
| 19 | 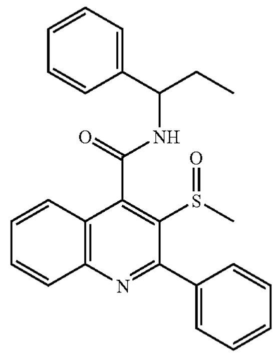 | (3-methylsulfinyl)-2-phenyl-N-(1-phenylpropyl)quinoline-4-carboxamide |
| 20 | 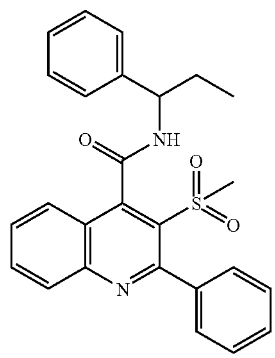 | 3-(methylsulfonyl)-2-phenyl-N-(1-phenylpropyl)quinoline-4-carboxamide |
| 21 | 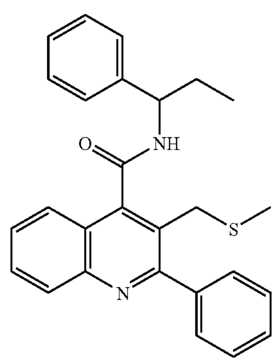 | 3-(methylthiomethyl)-2-phenyl-N-(1-phenylpropyl)quinoline-4-carboxamide |
| 22 | 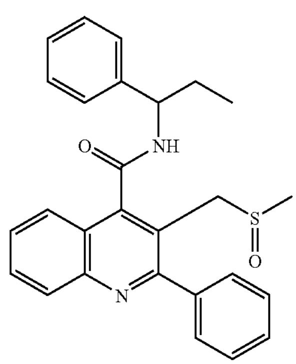 | 3-(methylsulfinylmethyl)-2-phenyl-N-(1-phenylpropyl)quinoline-4-carboxamide |

TABLE 1-continued

| Example | Structure | Name |
|---|---|---|
| 23 | 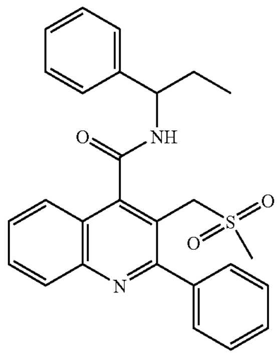 | 3-(methylsulfonylmethyl)-2-phenyl-N-(1-phenylpropyl)quinoline-4-carboxamide |
| 24 | 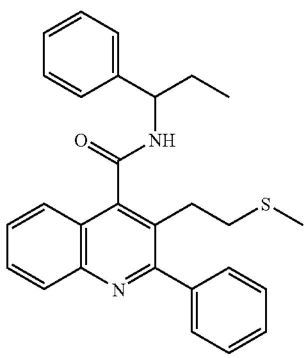 | 3-(2-(methylthio)ethyl)-2-phenyl-N-(1-phenylpropyl)quinoline-4-carboxamide |
| 25 | 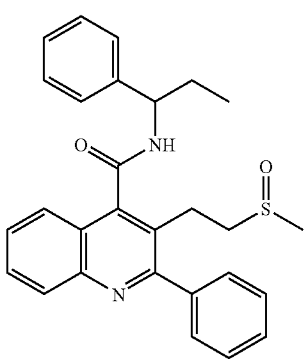 | 3-(2-(methylsulfinyl)ethyl)-2-phenyl-N-(1-phenylpropyl)quinoline-4-carboxamide |
| 26 | 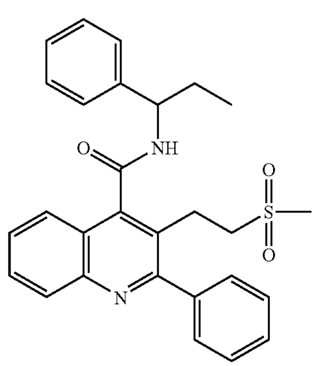 | 3-(2-(methylsulfonyl)ethyl)-2-phenyl-N-(1-phenylpropyl)quinoline-4-carboxamide |

TABLE 1-continued
| Example | Structure | Name |
|---|---|---|
| 27 | 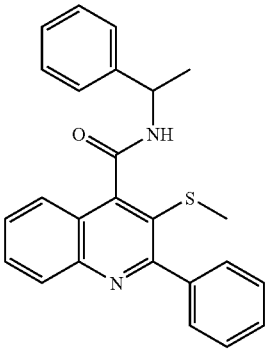 | 3-(methylthio)-2-phenyl-N-(1-phenylethyl)quinoline-4-carboxamide |
| 28 | 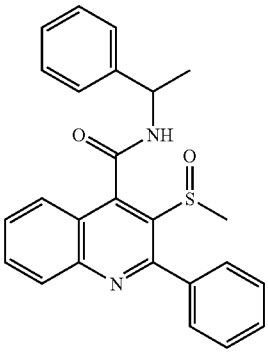 | 3-(methylsulfinyl)-2-phenyl-N-(1-phenylethyl)quinoline-4-carboxamide |
| 29 | 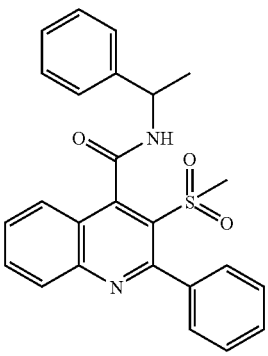 | 3-(methylsulfonyl)-2-phenyl-N-(1-phenylethyl)quinoline-4-carboxamide |
| 30 | 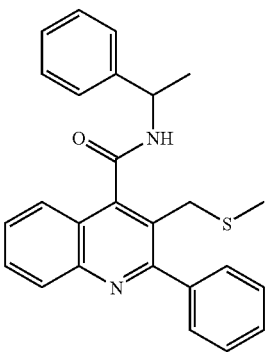 | 3-(methylthiomethyl)-2-phenyl-N-(1-phenylethyl)quinoline-4-carboxamide |

TABLE 1-continued

| Example | Structure | Name |
|---|---|---|
| 31 | 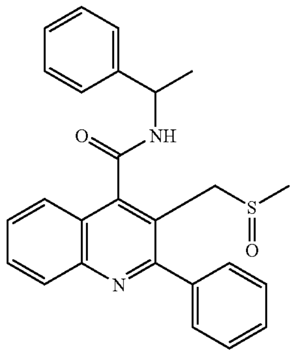 | 3-(methylsulfinylmethyl)-2-phenyl-N-(1-phenylethyl)quinoline-4-carboxamide |
| 32 | 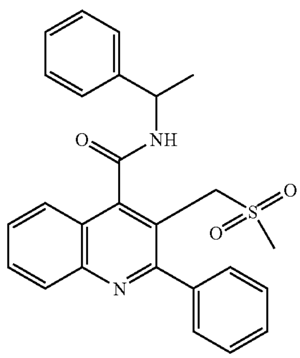 | 3-(methylsulfonylmethyl)-2-phenyl-N-(1-phenylethyl)quinoline-4-carboxamide |
| 33 | 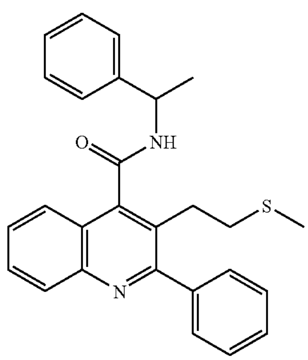 | 3-(2-(methylthio)ethyl)-2-phenyl-N-(1-phenylethyl)quinoline-4-carboxamide |
| 34 | 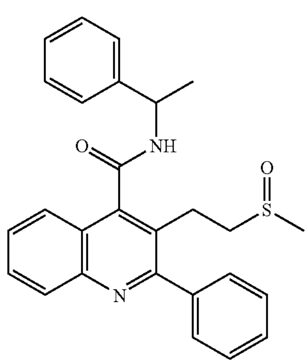 | 3-(2-(methylsulfinyl)ethyl)-2-phenyl-N-(1-phenylethyl)quinoline-4-carboxamide |

TABLE 1-continued

| Example | Structure | Name |
|---|---|---|
| 35 | 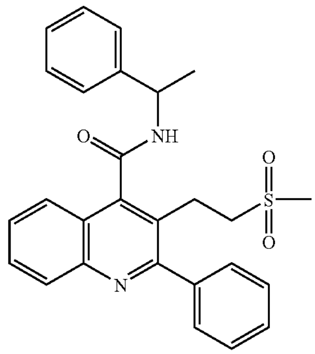 | 3-(2-(methylsulfonyl)ethyl)-2-phenyl-N-(1-phenylethyl)quinoline-4-carboxamide |
| 36 | 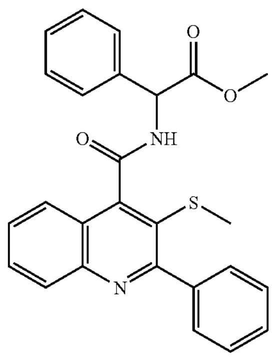 | methyl-2-(3-(methylthio)-2-phenylquinoline-4-carboxamido)-2-phenylethanoate |
| 37 | 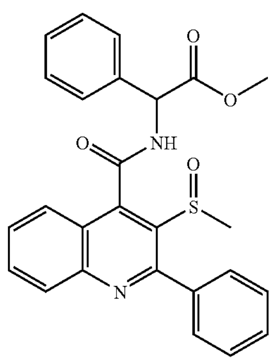 | methyl 2-(3-(methylsulfinyl)-2-phenylquinoline-4-carboxamido)-2-phenylethanoate |
| 38 | 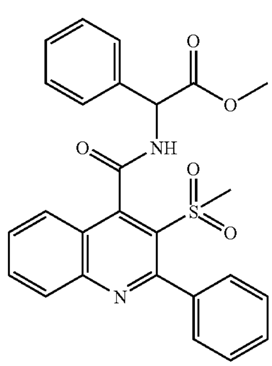 | methyl-2-(3-(methylsulfonyl)-2-phenylquinoline-4-carboxamido)-2-phenylethanoate |

TABLE 1-continued

| Example | Structure | Name |
|---|---|---|
| 39 | 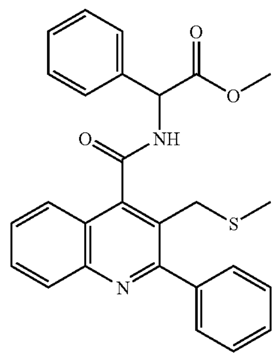 | methyl-2-(3-(methylthiomethyl)-2-phenylquinoline-4-carboxamido)-2-phenylethanoate |
| 40 | 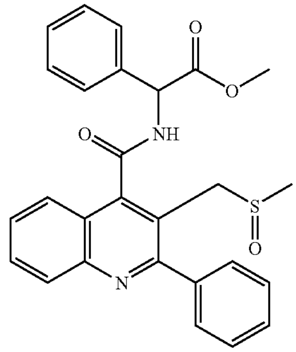 | methyl 2-(3-(methylsulfinylmethyl)-2-phenylquinoline-4-carboxamido)-2-phenylethanoate |
| 41 | 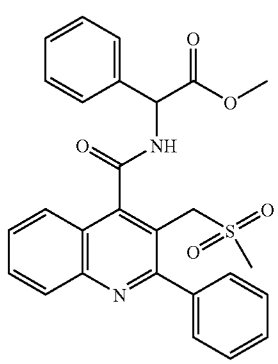 | methyl 2-(3-(methylsulfonylmethyl)-2-phenylquinoline-4-carboxamido)-2-phenylethanoate |
| 42 | 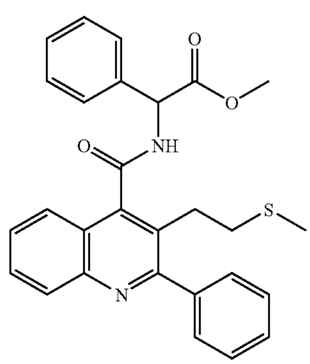 | methyl 2-(3-(2-(methylthio)ethyl)-2-phenylquinoline-4-carboxamido)-2-phenylethanoate |

TABLE 1-continued

| Example | Structure | Name |
|---------|-----------|------|
| 43 | 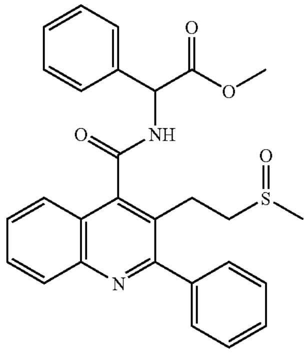 | methyl 2-(3-(2-(methylsulfinyl)ethyl)-2-phenylquinoline-4-carboxamido)-2-phenylethanoate |
| 44 | 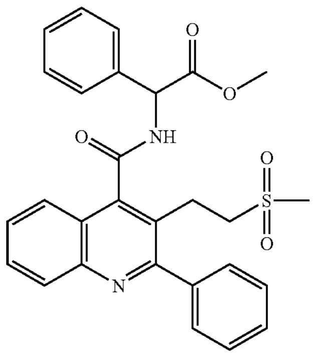 | methyl 2-(3-(2-(methylsulfonyl)ethyl)-2-phenylquinoline-4-carboxamido)-2-phenylethanoate |
| 45 | 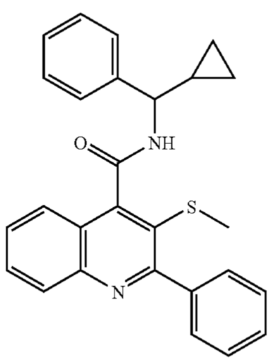 | N-(cyclopropyl(phenyl)methyl)-3-(methylthio)-2-phenylquinoline-4-carboxamide |
| 46 | 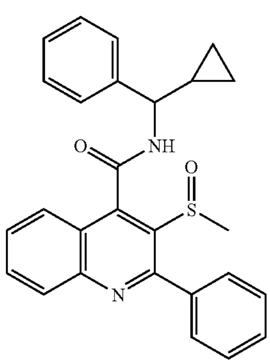 | N-(cyclopropyl(phenyl)methyl)-3-(methylsulfinyl)-2-phenylquinoline-4-carboxamide |

TABLE 1-continued

| Example | Structure | Name |
|---|---|---|
| 47 | 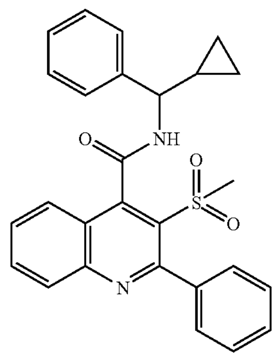 | N-(cyclopropyl(phenyl)methyl)-3-(methylsulfonyl)-2-phenylquinoline-4-carboxamide |
| 48 | 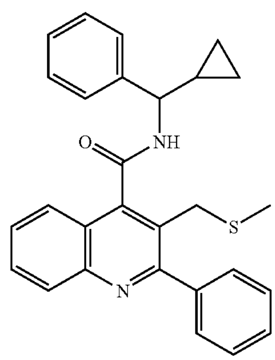 | N-(cyclopropyl(phenyl)methyl)-3-(methylthiomethyl)-2-phenylquinoline-4-carboxamide |
| 49 | 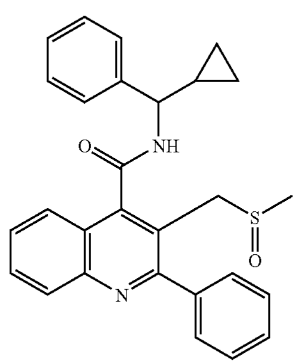 | N-(cyclopropyl(phenyl)methyl)-3-(methylsulfinylmethyl)-2-phenylquinoline-4-carboxamide |
| 50 | 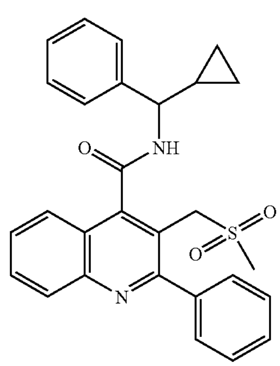 | N-(cyclopropyl(phenyl)methyl)-3-(methylsulfonylmethyl)-2-phenylquinoline-4-carboxamide |

TABLE 1-continued

| Example | Structure | Name |
|---|---|---|
| 51 | 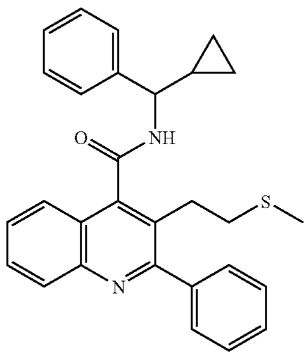 | N-(cyclopropyl(phenyl)methyl)-3-(2-(methylthio)ethyl)-2-phenylquinoline-4-carboxamide |
| 52 | 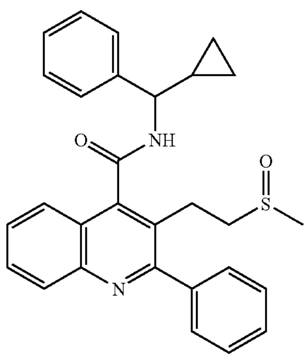 | N-(cyclopropyl(phenyl)methyl)-3-(2-(methylsulfinyl)ethyl)-2-phenylquinoline-4-carboxamide |
| 53 | 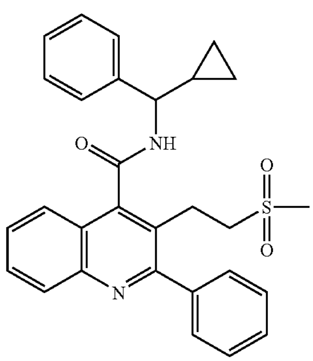 | N-(cyclopropyl(phenyl)methyl)-3-(2-(methylsulfonyl)ethyl)-2-phenylquinoline-4-carboxamide |
| 54 | 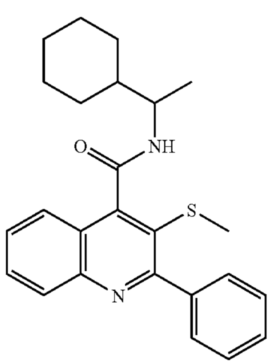 | N-(1-cyclohexylethyl)-3-(methylthio)-2-phenylquinoline-4-carboxamide |

TABLE 1-continued
| Example | Structure | Name |
|---|---|---|
| 55 | 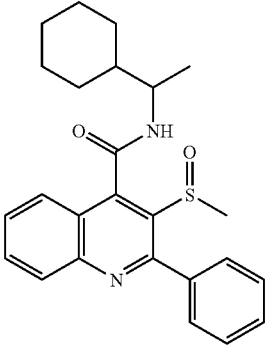 | N-(1-cyclohexylethyl)-3-(methylsulfinyl)-2-phenylquinoline-4-carboxamide |
| 56 | 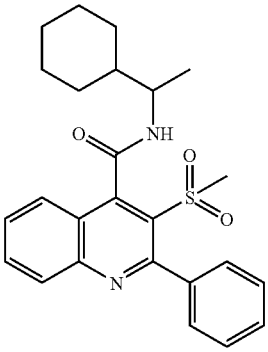 | N-(1-cyclohexylethyl)-3-(methylsulfonyl)-2-phenylquinoline-4-carboxamide |
| 57 | 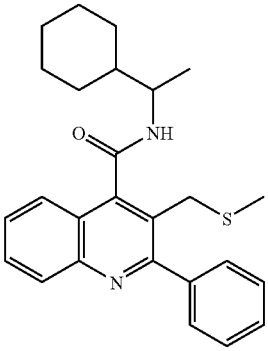 | N-(1-cyclohexylethyl)-3-(methylthiomethyl)-2-phenylquinoline-4-carboxamide |
| 58 | 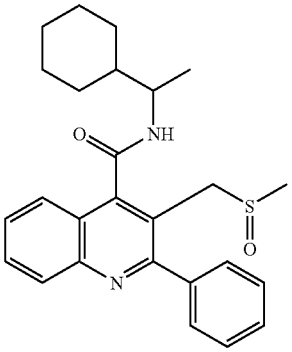 | N-(1-cyclohexylethyl)-3-(methylsulfinylmethyl)-2-phenylquinoline-4-carboxamide |

TABLE 1-continued
| Example | Structure | Name |
|---|---|---|
| 59 | 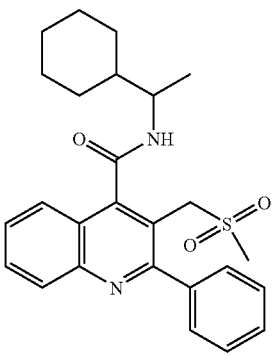 | N-(1-cyclohexylethyl)-3-(methylsulfonylmethyl)-2-phenylquinoline-4-carboxamide |
| 60 | 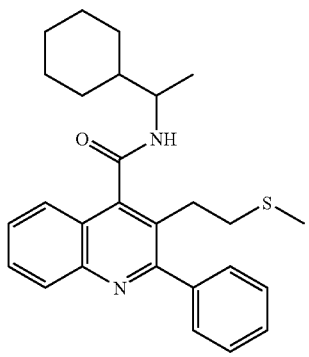 | N-(1-cyclohexylethyl)-3-(2-(methylthio)ethyl)-2-phenylquinoline-4-carboxamide |
| 612 | 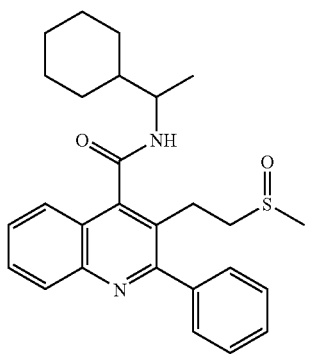 | N-(1-cyclohexylethyl)-3-(2-(methylsulfinyl)ethyl)-2-phenylquinoline-4-carboxamide |
| 62 | 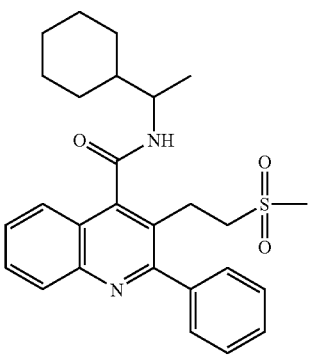 | N-(1-cyclohexylethyl)-3-(2-(methylsulfonyl)ethyl)-2-phenylquinoline-4-carboxamide |

TABLE 1-continued

| Example | Structure | Name |
|---|---|---|
| 63 | 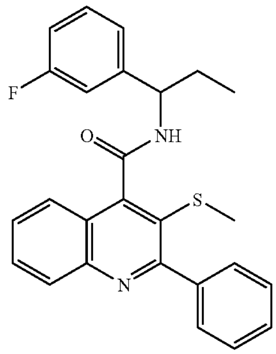 | N-(1-(3-fluorophenyl)propyl)-3-(methylthio)-2-phenylquinoline-4-carboxamide |
| 64 | 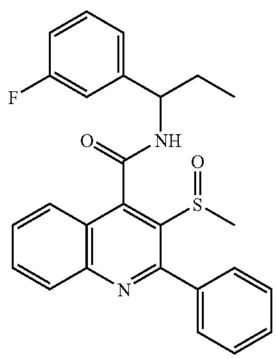 | N-(1-(3-fluorophenyl)propyl)-3-(methylsulfinyl)-2-phenylquinoline-4-carboxamide |
| 65 | 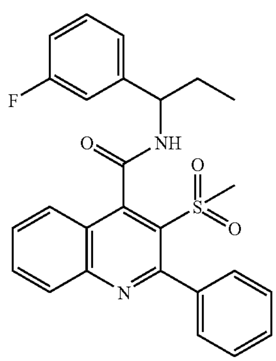 | N-(1-(3-fluorophenyl)propyl)-3-(methylsulfonyl)-2-phenylquinoline-4-carboxamide |
| 66 | 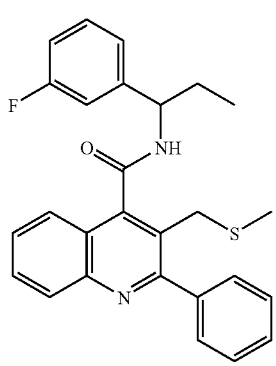 | N-(1-(3-fluorophenyl)propyl)-3-(methylthiomethyl)-2-phenylquinoline-4-carboxamide |

TABLE 1-continued
| Example | Structure | Name |
|---|---|---|
| 67 | 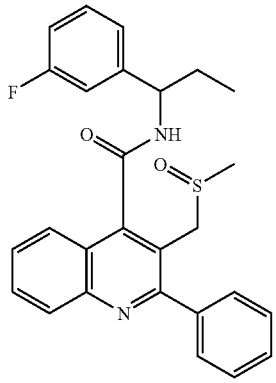 | N-(1-(3-fluorophenyl)propyl)-3-(methylsulfinylmethyl)-2-phenylquinoline-4-carboxamide |
| 68 | 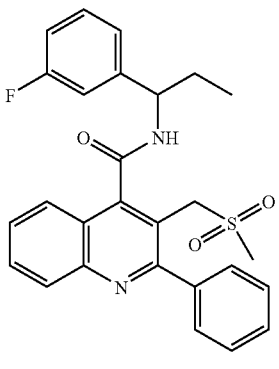 | N-(1-(3-fluorophenyl)propyl)-3-(methylsulfonylmethyl)-2-phenylquinoline-4-carboxamide |
| 69 | 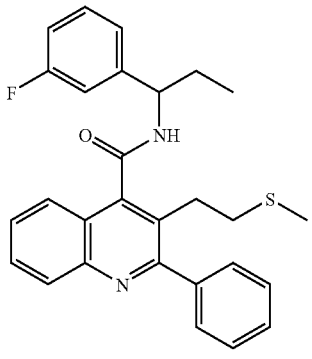 | N-(1-(3-fluorophenyl)propyl)-3-(2-(methylthio)ethyl)-2-phenylquinoline-4-carboxamide |
| 70 | 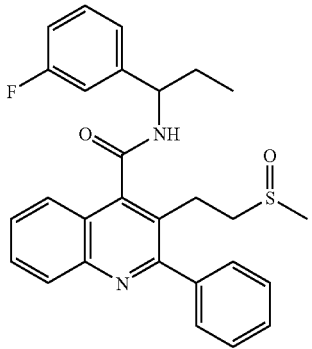 | N-(1-(3-fluorophenyl)propyl)-3-(2-(methylsulfinyl)ethyl)-2-phenylquinoline-4-carboxamide |

TABLE 1-continued

| Example | Structure | Name |
| --- | --- | --- |
| 71 | 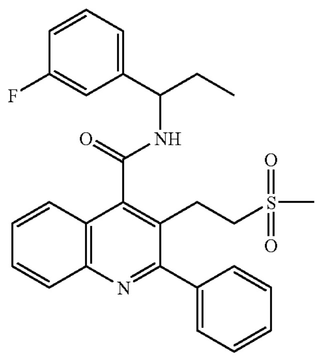 | N-(1-(3-fluorophenyl)propyl)-3-(2-(methylsulfonyl)ethyl)-2-phenylquinoline-4-carboxamide |
| 72 | 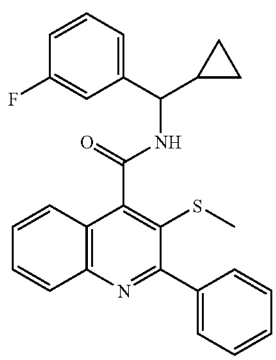 | N-(cyclopropyl(3-fluorophenyl)methyl)-3-(methylthio)-2-phenylquinoline-4-carboxamide |
| 73 | 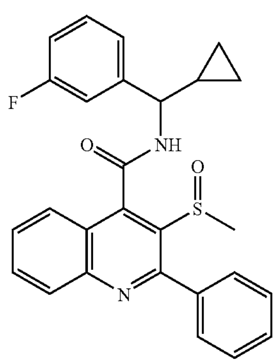 | N-(cyclopropyl(3-fluorophenyl)methyl)-3-(methysulfinyl)-2-phenylquinoline-4-carboxamide |
| 74 | 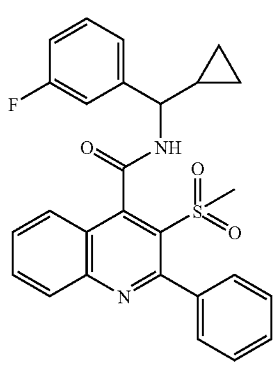 | N-(cyclopropyl(3-fluorophenyl)methyl)-3-(methylsulfonyl)-2-phenylquinoline-4-carboxamide |

TABLE 1-continued

| Example | Structure | Name |
|---|---|---|
| 75 | 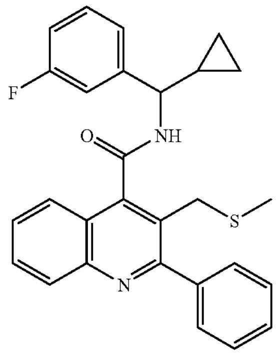 | N-(cyclopropyl(3-fluorophenyl)methyl)-3-(methylthiomethyl)-2-phenylquinoline-4-carboxamide |
| 76 | 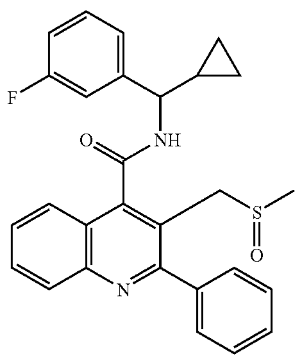 | N-(cyclopropyl(3-fluorophenyl)methyl)-3-(methylsulfinylmethyl)-2-phenylquinoline-4-carboxamide |
| 77 | 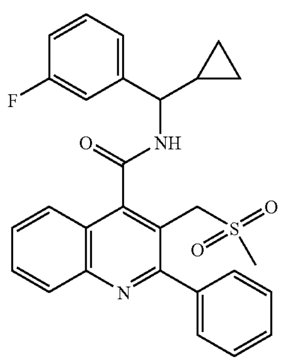 | N-(cyclopropyl(3-fluorophenyl)methyl)-3-(methylsulfonylmethyl)-2-phenylquinoline-4-carboxamide |
| 78 | 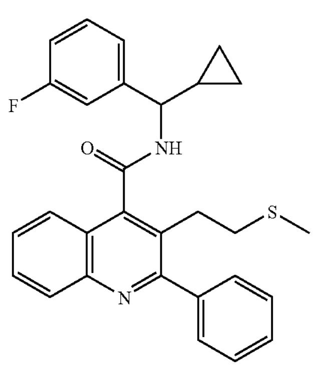 | N-(cyclopropyl(3-fluorophenyl)methyl)-3-(2-(methylthio)ethyl)-2-phenylquinoline-4-carboxamide |

TABLE 1-continued

| Example | Structure | Name |
|---------|-----------|------|
| 79 | 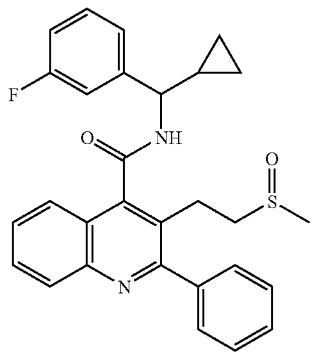 | N-(cyclopropyl(3-fluorophenyl)methyl)-3-(2-(methylsulfinyl)ethyl)-2-phenylquinoline-4-carboxamide |
| 80 | 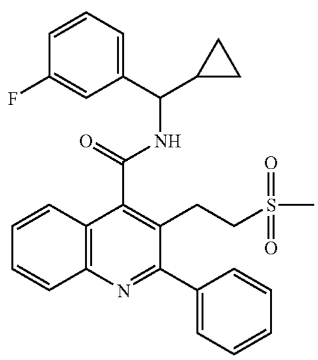 | N-(cyclopropyl(3-fluorophenyl)methyl)-3-(2-(methylsulfonyl)ethyl)-2-phenylquinoline-4-carboxamide |
| 81 | 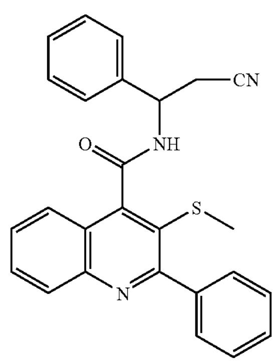 | N-(2-cyano-1-phenylethyl)-3-(methylthio)-2-phenylquinoline-4-carboxamide |
| 82 | 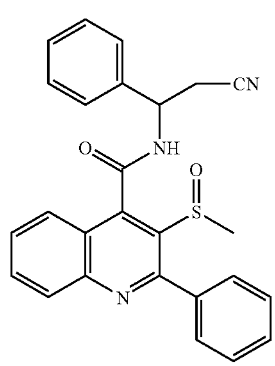 | N-(2-cyano-1-phenylethyl)-3-(methylsulfinyl)-2-phenylquinoline-4-carboxamide |

TABLE 1-continued

| Example | Structure | Name |
| --- | --- | --- |
| 83 | 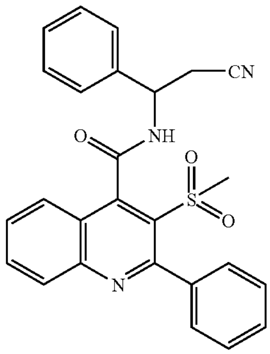 | N-(2-cyano-1-phenylethyl)-3-(methylsulfonyl)-2-phenylquinoline-4-carboxamide |
| 84 | 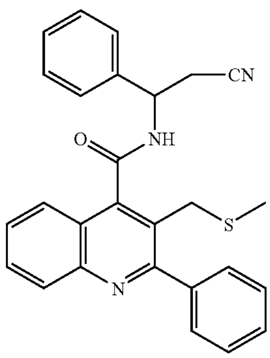 | N-(2-cyano-1-phenylethyl)-3-(methylthiomethyl)-2-phenylquinoline-4-carboxamide |
| 85 | 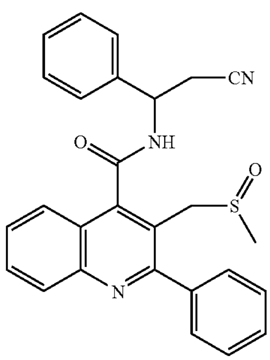 | N-(2-cyano-1-phenylethyl)-3-(methylsulfinylmethyl)-2-phenylquinoline-4-carboxamide |
| 86 | 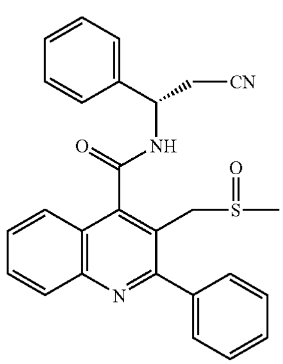 | N-((S)-2-cyano-1-phenylethyl)-3-(methylsulfinylmethyl)-2-phenylquinoline-4-carboxamide |

TABLE 1-continued

| Example | Structure | Name |
| --- | --- | --- |
| 87 | 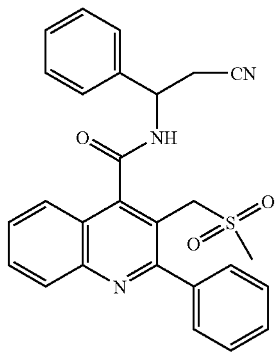 | N-(2-cyano-1-phenylethyl)-3-(methylsulfonylmethyl)-2-phenylquinoline-4-carboxamide |
| 88 | 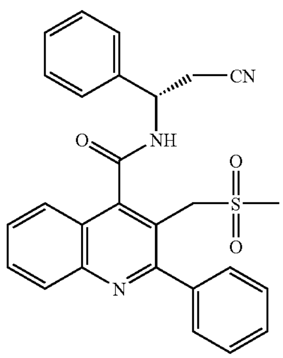 | N-((S)-2-cyano-1-phenylethyl)-3-(methylsulfonylmethyl)-2-phenylquinoline-4-carboxamide |
| 89 | 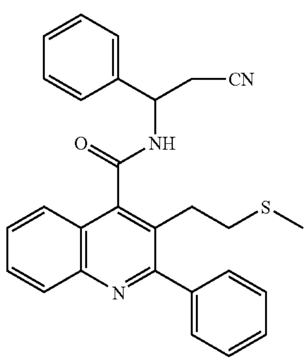 | N-(2-cyano-1-phenylethyl)-3-(2-(methylthio)ethyl)-2-phenylquinoline-4-carboxamide |
| 90 | 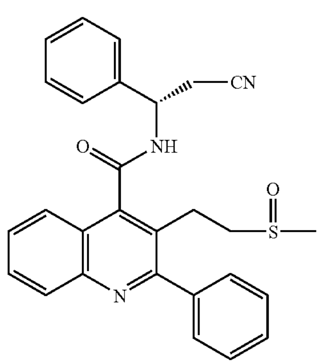 | N-((S)-2-cyano-1-phenylethyl)-3-(2-(methylsulfinyl)ethyl)-2-phenylquinoline-4-carboxamide |

TABLE 1-continued

| Example | Structure | Name |
|---|---|---|
| 91 | 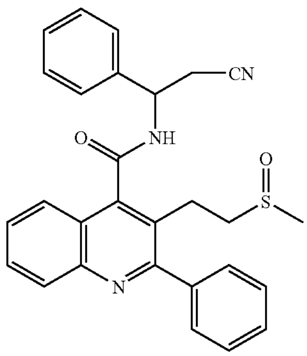 | N-(2-cyano-1-phenylethyl)-3-(2-(methylsulfinyl)ethyl)-2-phenylquinoline-4-carboxamide |
| 92 | 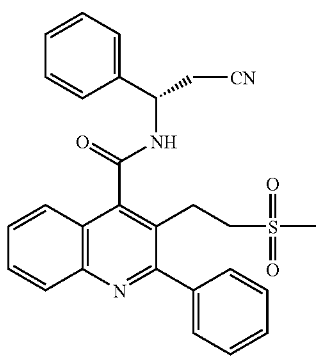 | N-((S)-2-cyano-1-phenylethyl)-3-(2-(methylsulfonyl)ethyl)-2-phenylquinoline-4-carboxamide |
| 93 | 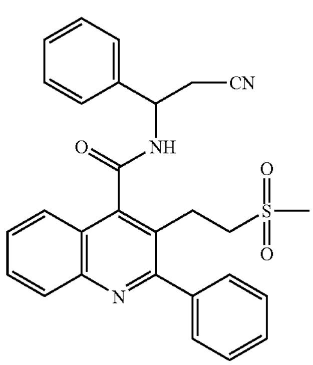 | N-(2-cyano-1-phenylethyl)-3-(2-(methylsulfonyl)ethyl)-2-phenylquinoline-4-carboxamide |

Example 88

N-[(1S)-2-cyano-1-phenylethyl]-3-[(methylsulfonyl)methyl]-2-phenylquinoline-4-carboxamide (5)

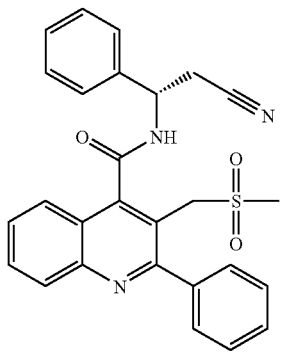

The compound of Example 88 was prepared in accord with the following Scheme:

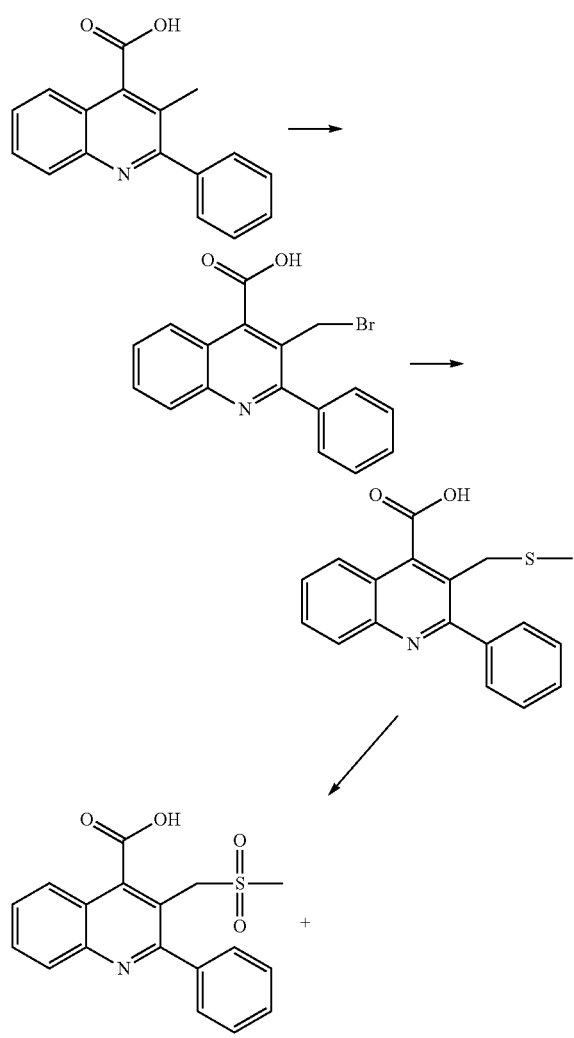

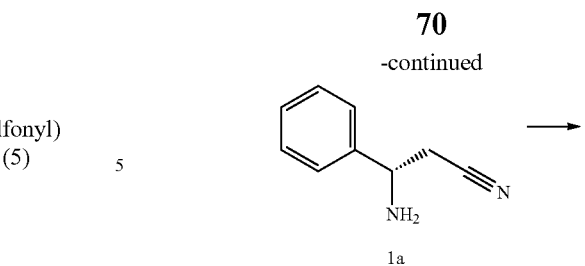

(a) 3-(Bromomethyl)-2-phenylquinoline-4-carboxylic acid

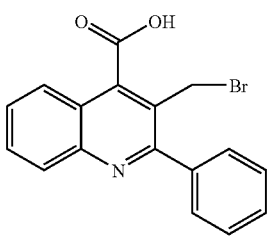

To a solution of 3-methyl-2-phenylquinoline-4-carboxylic acid (1.5 g, 5.7 mmol) and N-bromosuccinimide (1.52 g, 8.5 mmol) in carbon tetrachloride (25 mL) was added benzoyl peroxide (approximately 10 mg) and heated under reflux with illumination using a long wavelength ultraviolet lamp (Blak-ray model B100-AP, Upland, Calif.). After 4 h, additional portions of N-bromosuccinimide (750 mg, 4.2 mmol) and benzoyl peroxide (approximately 10 mg) were added. After an additional 2 h, the cooled mixture was diluted with water. Sodium thiosulfate (1 g) was added, then the pH was adjusted to approximately 4.0 by addition of dilute HCl and NaOH. The mixture was further diluted with ethyl acetate, extracted, and dried (MgSO$_4$) to afford the product as a light brown powder (1.62 g, 6.2 mmol). $^1$H NMR (300 MHz, DMSO) δ

8.09 (d, J=8.4 Hz, 1H), 7.96-7.86 (m, 2H), 7.76 (d, J=8.2 Hz, 1H), 7.68-7.64 (m, 2H), 7.61-7.55 (m, 3H), 4.75 (s, 2H). LRMS m/z 342.0.

(b) 3-[(Methylsulfanyl)methyl]-2-phenylquinoline-4-carboxylic acid

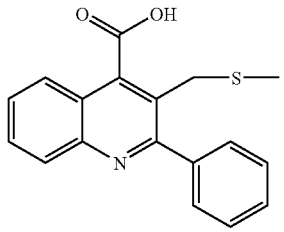

To a solution of 3-(Bromomethyl)-2-phenylquinoline-4-carboxylic acid (650 mg, 1.9 mmol) in tetrahydrofuran (40 mL) was added sodium methanethiolate (400 mg, 5.7 mmol). The mixture was stirred overnight, concentrated, diluted with pH 4 buffer (40 mL) and ethyl acetate (40 mL), and extracted. The organic phase was dried (MgSO$_4$), and concentrated to afford the desired product as a brown oil which was used without purification.

(c). 3-[(Methanesulfonyl)methyl]-2-phenylquinoline-4-carboxylic acid

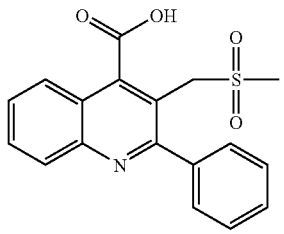

A solution of 3-[(methylsulfanyl)methyl]-2-phenylquinoline-4-carboxylic acid (450 mg, 1.5 mmol) in THF (2 mL) was added to a solution of NaIO$_4$ (400 mg, 1.9 mmol) at 0° C. This mixture was stirred for 2 h while allowing it warm to room temperature to afford a mixture of the sulfoxide and the sulfone. The mixture was concentrated and purified by preparative reverse phase HPLC, then lyophilized to afford the desired product as a white powder (135 mg, 0.40 mmol). $^1$H NMR (300.132 MHz, DMSO) δ 8.12-8.09 (m, 2H), 7.90 (t, J=7.2 Hz, 1H), 7.76 (t, J=7.4 Hz, 1H), 7.63-7.53 (m, 5H), 4.89 (s, 2H), 2.73 (s, 3H); LRMS m/z/z 342.1

(d) To prepare the title compound, a solution of 3-methanesulfonylmethyl-2-phenylquinoline-4-carboxylic acid (100 mg, 0.32 mmol) in methylene chloride (5 mL) was added oxalyl chloride (28 μL, 0.32 mmol) and dimethyl formamide (approximately 1 μL). After stirring for 3 h, the reaction mixture was concentrated and re-dissolved in methylene chloride (5 mL). Triethylamine (135 μL, 0.97 mmol) and (S)-3-amino-3-phenyl-propionitrile (1a) were added. After stirring for 4 h the mixture was concentrated and purified by preparative reverse phase chromatography using a gradient elution of water and acetonitrile with 0.1% trifluoroacetic acid. Following lyophilization, the desired product was obtained as the trifluoroacetate salt (8 mg, 0.017 mmol). $^1$H NMR (300 MHz, DMSO) δ 9.76 (d, J=8.0 Hz, 1H), 8.08 (d, J=8.2 Hz, 1H), 7.86 (s, 1H), 7.56-7.40 (m, 11H), 5.60 (s, 1H), 4.96-4.60 (m, 2H), 3.19 (s, 2H), 3.19 (s, 3H). HRMS m/z 470.1507, calcd for C$_{27}$H$_{23}$N$_3$O$_3$S 470.1538.

Biological Tests
NK-3 Receptor Binding Activity:

Generally, NK-3r binding activity may be assessed using assays performed as described in Krause et al., (Proc. Natl. Acad. Sci. USA 94: 310-315, 1997). NK-3r complementary DNA is cloned from human hypothalamic RNA using standard procedures. The receptor cDNA is inserted into a suitable expression vector transfected into a Chinese hamster ovary cell line, and a stably-expressing clonal cell line may be isolated, characterized and used for experiments.

Cells may be grown in tissue culture medium by techniques known to those of skill in the art and recovered by low speed centrifugation. Cell pellets may be homogenized, total cellular membranes isolated by high speed centrifugation and suspended in buffered saline. Generally, receptor binding assays may be performed by incubating suitable amounts of purified membrane preparations with $^{125}$I-methylPhe7-neurokinin B, in the presence or absence of test compounds. Membrane proteins may be harvested by rapid filtration and radioactivity may be quantitated in a β-plate scintillation counter. Nonspecific binding may be distinguished from specific binding by use of suitable controls and the affinity of compounds for the expressed receptor may be determined by using different concentrations of compounds.

Preparation of Membranes from CHO Cells Transfected with Cloned NK-3 Receptors:

A human NK-3 receptor gene was cloned using methods similar to those described for other human NK receptors (Aharony et al., Mol. Pharmacol. 45:9-19, 1994; Caccese et al., Neuropeptides 33, 239-243, 1999). The DNA sequence of the cloned NK-3 receptor differed from the published sequence (Buell et al., FEBS Letts. 299, 90-95, 1992; Huang et al., Biochem. Biophys. Res. Commun. 184, 966-972, 1992) having a silent single T>C base change at nucleotide 1320 of the coding sequence. Since the change is silent, the cloned gene provides a primary amino acid sequence for the encoded NK-3 receptor protein identical to the published sequence. The receptor cDNA was used to transfect CHO-K1 cells using standard methods and a clone stably-expressing the receptor was isolated and characterized. Plasma membranes from these cells were prepared as published (Aharony et al., 1994).

Cells were harvested and centrifuged to remove medium. The pelleted cells were homogenized (Brinkman Polytron, three 15 sec bursts on ice) in a buffer consisting of 50 mM Tris-HCl (pH 7.4), 120 mM NaCl, 5 mM KCl, 10 mM EDTA and protease inhibitors (0.1 mg/ml soybean trypsin inhibitor, and 1 mM iodoacetamide). The homogenate was centrifuged at 1000×g for 10 min at 4° C. to remove cell debris. Pellets were washed once with homogenizing buffer. Supernatants were combined and centrifuged at 40,000×g for 20 min at 4° C. The membrane-containing pellet was homogenized with a Polytron as before. The suspension was centrifuged at 40,000×g for 20 min at 4° C., the pellet suspended in buffer (20 mM HEPES, pH 7.4 containing 3 mM MgCl$_2$, 30 mM KCl, and 100 μM thiorphan) and the protein concentration determined. The membrane suspension was then diluted to 3 mg/ml with buffer containing 0.02% BSA, and flash frozen. Samples were stored at −80° C. until used.

Assay for NK-3 Receptor Binding Activity:

A receptor binding assay method with [$^{125}$I]-MePhe7-NKB was modified from that described by Aharony et al., J. Pharmacol. Exper. Ther., 274:1216-1221, 1995.

Competition experiments were carried out in 0.2 mL assay buffer (50 mM Tris-HCl, 4 mM $MnCl_2$, 10 µM thiorphan, pH 7.4) containing membranes (2 µg protein/reaction), tested competitors, and [$^{125}$I]-MePhe7NKB (0.2 nM). Unlabeled homologue ligand (0.5 µM) was used to define nonspecific binding. Incubations were carried out at 25° C. for 90 min. Receptor-bound ligand was isolated by vacuum filtration in a Packard Harvester onto GF/C plates presoaked in 0.5% BSA. Plates were washed with 0.02 M Tris, pH 7.4. Computation of equilibrium binding constants ($K_D$ and Ki), receptor density (1max), and statistical analysis was carried out as published previously (Aharony et al., 1995) using GraphPad Prism or IDBS XLfit software.

NK-3 Functional Activity:

Generally, NK-3 functional activity may be assessed by using calcium mobilization assays in stable NK-3r-expressing cell lines. Calcium mobilization induced by the methylPhe7-neurokinin B agonist may be monitored using a FLIPR (Molecular Devices) instrument in the manner described by the manufacturer. Agonists may be added to the cells and fluorescence responses continuously recorded for up to 5 min. The actions of antagonists may be assessed by preincubating cells prior to administration of the methylPhe7-neurokinin B agonist. The action of agonists may be assessed by observing their intrinsic activity in such a system.

Assay for NK-3 Functional Activity:

NK-3 receptor expressing CHO cells were maintained in growth media (Ham's F12 medium, 10% FBS, 2 mM L-glutamine, and 50 mg/mL Hygromycin B). One day prior to the assay cells were dispensed into 384-well plates in Ultraculture media (Cambrex Bio Science) with 2 mM L-glutamine to achieve 70-90% confluency. To quantify NK-3 receptor-induced calcium mobilization, cells were first washed with assay buffer consisting of Hanks' Balanced Salt Solution, 15 mM HEPES, and 2.5 mM probenecid, pH 7.4. The cells were then loaded with Fluo4/AM dye (4.4 µM in assay buffer. Cells were incubated for one hour and then washed with assay buffer, exposed to 0.02-300 nM senktide and the fluorescence response recorded using a FLIPR instrument (Molecular Devices Corporation). To quantify antagonism of the agonist response, cells were preincubated with varying concentrations of test compound for 2-20 min and then exposed to 2 nM senktide, a concentration that alone elicits about an 70% maximal calcium response. The resulting data was analyzed using XLfit software (IDBS manufacturer) to determine EC50 and IC50 values.

The invention claimed is:

1. 3-[(methylsulfinyl)methyl]-2-phenyl-N-[(1S)-1-phenylpropyl]quinoline-4-carboxamide or a diastereomer or a pharmaceutically acceptable salt thereof.

2. A diastereomer of 3-[(methylsulfinyl)methyl]-2-phenyl-N-[(1S)-1-phenylpropyl]quinoline-4-carboxamide or a pharmaceutically acceptable salt thereof.

3. A pharmaceutical composition comprising a pharmaceutically acceptable diluent, lubricant or carrier, and a therapeutically effective amount of the compound according to claim 1.

4. A pharmaceutical composition comprising a pharmaceutically acceptable diluent, lubricant or carrier, and a therapeutically effective amount of a diastereomer according to claim 2.

5. A method of treatment of a disease or condition in which modulation of the NK-3 receptor is beneficial which method comprises administering to a subject suffering from said disease or condition a therapeutically effective amount of the compound according to claim 1, wherein said disease or condition is selected from depression, anxiety, schizophrenia, cognitive disorders, psychoses, obesity, inflammatory diseases, irritable bowel syndrome, inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer.

6. A method of treatment of a disease or condition in which modulation of the NK-3 receptor is beneficial which method comprises administering to a subject suffering from said disease or condition a therapeutically-effective amount of a diastereomer according to claim 2, wherein said disease or condition is selected from depression, anxiety, schizophrenia, cognitive disorders, psychoses, obesity, inflammatory diseases, irritable bowel syndrome, inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer.

7. A method of treatment of a disease or condition in which modulation of the NK-3 receptor is beneficial which method comprises administering to a subject suffering from said disease or condition a therapeutically effective amount of a pharmaceutical composition according to claim 3, wherein said disease or condition is selected from depression, anxiety, schizophrenia, cognitive disorders, psychoses, obesity, inflammatory diseases, irritable bowel syndrome, inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer.

8. A method of treatment of a disease or condition in which modulation of the NK-3 receptor is beneficial which method comprises administering to a subject suffering from said disease or condition a therapeutically effective amount of a pharmaceutical composition according to claim 4, wherein said disease or condition is selected from depression, anxiety, schizophrenia, cognitive disorders, psychoses, obesity, inflammatory diseases, irritable bowel syndrome, inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer.

* * * * *